(12) United States Patent
Oreffo et al.

(10) Patent No.: US 11,173,230 B2
(45) Date of Patent: Nov. 16, 2021

(54) POLYMER-CLAY COMPOSITE AND ORGANOCLAY

(71) Applicant: University of Southampton, Southampton (GB)

(72) Inventors: Richard Oreffo, Southampton (GB); Jonathan Dawson, Southampton (GB); David Gibbs, Southampton (GB); Jons Hilborn, Southampton (GB); Dmitri Ossipov, Southampton (GB)

(73) Assignee: University of Southampton, Southampton (GB)

( * ) Notice: Subject to any disclaimer, the term of this patent is extended or adjusted under 35 U.S.C. 154(b) by 0 days.

(21) Appl. No.: 16/274,047

(22) Filed: Feb. 12, 2019

(65) Prior Publication Data

US 2019/0247542 A1    Aug. 15, 2019

Related U.S. Application Data

(63) Continuation of application No. 15/306,020, filed as application No. PCT/GB2015/051212 on Apr. 24, 2015, now Pat. No. 10,245,350.

(30) Foreign Application Priority Data

Apr. 24, 2014 (GB) .................... 1407248

(51) Int. Cl.
  *C08K 3/34*   (2006.01)
  *A61L 27/44*  (2006.01)
  (Continued)

(52) U.S. Cl.
  CPC ........ *A61L 27/446* (2013.01); *A61K 38/1875* (2013.01); *A61K 47/02* (2013.01); *A61L 27/52* (2013.01); *A61L 27/54* (2013.01); *C08J 3/075* (2013.01); *C08K 3/346* (2013.01); *A61L 2300/414* (2013.01); *A61L 2300/64* (2013.01);
  (Continued)

(58) Field of Classification Search
  None
  See application file for complete search history.

(56) References Cited

U.S. PATENT DOCUMENTS

| 2004/0005993 | A1* | 1/2004 | Hartshorn | ............ C11D 3/3776 510/445 |
| 2008/0039570 | A1* | 2/2008 | Bhiwankar | ............ B29C 48/08 524/447 |
| 2017/0043058 | A1  | 2/2017 | Oreffo et al. | |

FOREIGN PATENT DOCUMENTS

CN   101703805   5/2010

OTHER PUBLICATIONS

Yang et al., Chern. Mater., 2012, 24(9), pp. 1690-1697. (Year: 2012).*

(Continued)

*Primary Examiner* — Brian Gulledge
(74) *Attorney, Agent, or Firm* — Armstrong Teasdale LLP

(57) ABSTRACT

The invention relates to a polymer-clay composite material comprising clay nanoparticles and a polymer, and wherein (a) the polymer comprises phosphate and/or phosphonate ligands; or (b) the polymer-clay composite further comprises linker molecules comprising a phosphate or phosphonate ligand, wherein the linker molecules are arranged to be anchored to the polymer. The invention further relates to organoclays, BMP-clay composite material. Uses, treatments, and manufacturer of the material are also provided.

14 Claims, 20 Drawing Sheets

(51) Int. Cl.
  A61L 27/52  (2006.01)
  A61L 27/54  (2006.01)
  C08J 3/075  (2006.01)
  A61K 38/18  (2006.01)
  A61K 47/02  (2006.01)
(52) U.S. Cl.
  CPC ....... *A61L 2400/12* (2013.01); *A61L 2430/02* (2013.01); *C08J 2305/08* (2013.01); *C08K 2201/006* (2013.01)

(56) References Cited

OTHER PUBLICATIONS

Supplemental information for Yang et al., Chem. Mater., 2012, 24(9), S1-S11. (Year: 2012).*
Dawson et al., Adv. Mater., 2013, 25(30), pp. 4069-4086. (Year: 2013).*
Amendment and Response to Non-Final Office Action dated Jul. 12, 2018 for U.S. Appl. No. 15/306,020.
Final Office Action dated Jul. 27, 2018 for U.S. Appl. No. 15/306,020.
International Search Report and Written Opinion dated Nov. 6, 2015 as received in PCT/GB2015/051212.
Akazawa, et al., "Biodegradation and bioabsorption innovation of the functionally graded bovine bone-originated apatite with blood permeability" Published online Oct. 4, 2005 in Wiley InterScience, pp. 44-51.
Akazawa, et al., "Osteoinduction by functionally Graded Apatites of Bovine Origin Loaded with Bone Morphogenetic Protein-2," The American Ceramic Society 88 [12] pp. 3545-3548 (2005).
Axelrad, et al., Heterotopic ossification after the use of commercially available recombinant human bone morphogenetic proteins in four patients, The Journal of Bone and Joint Surgery, vol. 90-B, No. 12, Dec. 2008, pp. 1617-1622.
Ben-David, et al., Low dose BMP-2 treatment for bone repair using a PEGylated fibrinogen hydrogel matrix, Biomaterials, 34, 2013, pp. 2902-2910.
Bessa, et al., "Silk Fibroin Microparticles as Carriers for Delivery of Human Recombinant Bone Morphogenetic Protein-2: In Vitro and In Vivo Bioactivity," Tissue Engineering: Part C, vol. 00, No. 00, 2010.
Bhakta, et al., "Hyaluronic acid-based hydrogels functionalized with heparin that support controlled release of bioactive BMP-2," Biomaterials 33 (2012) 6113-6122.
Bhakta, et al., "The influence of collagen and hyaluronan matrices on the delivery and bioactivity of bone morphogenetic protein-2 and ectopic bone formation" Acta Biomaterialia 9 (2013) pp. 9098-9106.
Blokhuis, et al., Autograft versus BMPs for the treatment of non-unions: What is the evidence?, Injury, Int. J. Care Injured 44, 2013, S1, S40-S42.
Boerckel, et al., Effects of protein dose and delivery system on BMP-mediated bone regeneration, Biomaterials, 32, 2011, pp. 5241-5251.
Dao, et al., "Bone regeneration using photocrosslinked hydrogel incorporating rhBMP-2 loaded 2-N, 6-O-sulfated chitosan nanoparticles," Biomaterials 35 (2014) 2730-2742.
Dhen, et al., "Homogeneous osteogenesis and bone regeneration by demineralized bone matrix loading with collagen-targeting bone morphogenetic protein-2," Biomaterials 28 (2007) 1027-1035.
Dawson, et al., Clay Gels for the Delivery of Regenerative Microenvironments, Adv. Matter, 2011, 23, pp. 3304-3308.
Dawson, et al., Clay: New Opportunities for Tissue Regeneration and Biomaterial Design, Adv. Matter, 2013, 25, pp. 4069-4086.
Dawson, et al., Recombinant Human BoneMorphogenetic Protein-2 on an Absorbable Collagen Sponge with an Osteoconductive Bulking Agent in Posterolateral Arthrodesis with Instrumentation, The Journal of Bone and Joint Surgery, Jul. 2009, vol. 91-A, No. 7, pp. 1604-1613.
Degat, et al., "Enhancement of the biological activity of BMP-2 by synthetic dextran derivatives," Published online Feb. 19, 2008 in Wiley InterScience, pp. 174-183.
Fischer, et al., A systematic review of comparative studies on bone graft alternatives for common spine fusion procedures, Springer-Verlag Berline Heidelberg, Eur Spine J, 2013, 22: 1423-1435.
Gaharwar, et al., Bioactive Silicate Nanoplatelets for Osteogenic Differentiation of Human Mesenchymal Stem Dells, Adv. Mater, 2013, 25, pp. 3329-3336.
Geuze, et al., "A Differential Effect of Bone Morphogenetic Protein-2 and Vascular Endothelial Growth Factor Release Timing on Osteogenesis at Ectopic and Orthotopic Sites in a Large-Animal," Tissue Engineering: Part A, vol. 18, Nos. 19 and 20, 2012.
Gibbs, et al., "Bone induction at physiological doses of BMP through localization by clay nanoparticle gels," Biomaterials 99 (2016) pp. 16-23.
Gibbs, et al., "Supplementary Table 1 for Bone induction at physiological doses of BMP through localization by clay nanoparticle gels," (2016) pp. 1-8.
Gibbs, et al., http://dx.doi.Org/10.1016/j.biomaterials.2016.05.010. "Bone induction at physiological doses of BMP through localization by clay nanoparticle gels," Biomaterials, vol. 99, Aug. 2016, pp. 16-23.
Gothard, et al., Tissue Engineered Bone Using Select Growth Factors: A Comprehensive Review of Animal Studies and Clinical Translation Studies in Man, European Cells and Materials, vol. 28, 2014, pp. 166-208.
Govender, et al., Recombinant Human Bone Morphogenetic Protein-2 for Treatment of Open Tibial Fractures, The Journal of Bone and Joint Surgery, Inc , Dec. 2002 vol. 84-A, No. 12., pp. 2123-2134.
Gruber, et al., "Ectopic bone formation after implantation of a slow release system of polylactid acid and rhBMP-2," John Wiley & Sons A/S, Clin. Oral Impl. Res. 20, 2009, 24-30.
Hamilton, et al., "Improved Bone Morphogenetic Protein-2 Retention in an Injectable Collagen Matrix Using Bifunctional Peptides," PLOS ONE www.plosone.org, Aug. 2013, vol. 8, Issue 8, e70715.
Hara, et al., "Effect of aging on the osteoinductive activity of recombinant human bone morphogenetic protein-2 in rats," Journal of Surgical Research, 195, (2015), pp. 377-383.
Helgeson, et al., Adjacent vertebral body osteolysis with bone morphogenetic protein use in transforaminal lumbar interbody fusion, The Spine Journal, 11, 2011, pp. 507-510.
Hulsart-Billström, et al., "Calcium phosphates compounds in conjunction with hydrogel as carrier for BMP-2: A study on ectopic bone formation in rats," Acta Biomaterialia 7 (2011) 3042-3049.
Hulsart-Billstrom, et al., "Morphological differences in BMP-2-induced ectopic bone between solid and crushed hyaluronan hydrogel templates," J Mater Sci: Mater Med (2013) 24:1201-1209.
Ishida, et al., "Cartilage oligomeric matrix protein enhances osteogenesis by directly binding and activating bone morphogenetic protein-2," www.elsevier.com/locate/bone, Bone 55 (2013) 23-35.
Isobe, et al., "Bone morphogenetic protein encapsulated with a biodegradable and biocompatible polymer," Journal ol Biomedical Materials Research, vol. 32, 433-438 (1996).
Isobe, et al., "The role of recombinant human bone morphogenetic protein-2 in PLGA capsules at an extraskeletal site of the rat," 1999 John Wiley & Sons, Inc. CCC 0021-9304/99/010036-06 pp. 36-41.
Jeon, et al., "Affinity-based growth factor delivery using biodegradable, photocrosslinked heparin-alginate hydrogels," J Control Release. Sep. 2, 2011; 154(3): 258-266. doi:10.1016/j-jconrel.2011.06.027.
Jeon, et al., "Enhancement of ectopic bone formation by bone morphogenetic protein-2 released from a heparin-conjugated poly(L-lactic-co-glycolic acid) scaffold," Biomaterials 28 (2007) 2763-2771.
Jeon, et al., "Long-term delivery enhances in vivo osteogenic efficacy of bone morphogenetic protein-2 compared to short term delivery," Biochemical and Biophysical Research Communications 369 (2008) 774-780.
Jin, et al., "Effects of geometry of hydroxyapatite as a cell substratum in BMP-induced ectopic bone formation," 2000 John Wiley & Sons, Inc. pages 491-499.

(56) References Cited

OTHER PUBLICATIONS

Kakudo, et al., "Effect of recombinant human fibroblast growth factor-2 on intramuscular ectopic osteoinduction by recombinant human bone morphogenetic protein-2 in rats," Wound Rep Reg (2006) 14, 336-342, by theWound Healing Society.

Katagiri, et al., "Bone Morphogenetic Protein-2 Converts the Differentiation Pathway of C2C12 Myoblasts into the Osteoblast Lineage," The Journal of Cell Biology, vol. 127, No. 6, Part 1, Dec. 1994, pp. 1755-1766.

Kato, et al., "Ectopic bone formation in mice associated with a lactic acid/dioxanone/ethylene glycol copolymertricalcium phosphate composite with added recombinant human bone morphogenetic protein-2." Biomaterials 27 (2006) 3927-3933.

Kato, et al., "Optimized use of a biodegradable polymer as a carrier material for the local delivery of recombinant human bone morphogenetic protein-2 (rhBMP-2)," Biomaterials 27 (2006) pp. 2035-2041.

Kempen, et al., "Effect of local sequential VEGF and BMP-2 delivery on ectopic and orthotopic bone regeneration," Biomaterials 30 (2009) 2816-2825.

Kempen, et al., "Enhanced Bone Morphogenetic Protein-2-lnduced Ectopic and Orthotopic Bone Formation by ntermittent Parathyroid Hormone (1-34) Administration," Tissue Engineering: Part A, vol. 16, No. 12, 2010.

Kempen, et al., "Retention of in vitro and in vivo BMP-2 bioactivities in sustained delivery vehicles for bone tissue engineering," Biomaterials 29 (2008) 3245-3252.

Kisiel, et al., "Complexation and Sequestration of BMP-2 from an ECM Mimetic Hyaluronan Gel for Improved Bone Formation," PLOS ONE, Oct. 2013, vol. 8, Issue 10, e78551.

Kisiel, et al., "Improving the osteogenic potential of BMP-2 with hyaluronic acid hydrogel modified with integrin-specific fibronectin fragment," Biomaterials 34 (2013) 704-712.

Kroese-Deutman, et al., "Bone inductive properties of rhBMP-2 loaded porous calcium phosphate cement implants inserted at an ectopic site in rabbits," Biomaterials 26 (2005) 1131-1138.

Kuboki, et al., "BMP-Induced osteogenesis on the surface of hydroxyapatite with geometrically feasible and nonfeasible structures: Topology of osteogenesis," 1998 John Wiley & Sons, Inc. CCC 0021-9304/98/020190-10, pp. 190-199.

Kuboki, et al., "Geometry of Carriers Controlling Phenotypic Expression in BMP-Induced Osteogenesis and Chondrogenesis," The Journal of Bone & Joint Surgery, vol. 83-A, Supplement 1, Part 2, 2001.

Lee, et al., "Controlled release of BMP-2 using a heparin-conjugated carrier system reduces in vivo adipose tissue formation," 2014 Wiley Periodicals, Inc. J Biomed Mater Res Part A 2015:103A:545-554.

Lee, et al., "The Efficacy of Porous Hydroxyapatite Granule as a Carrier of E.coli-derived Recombinant Human Bone Morphogenetic Protein-2," Tissue Engineering and Regenerative Medicine, vol. 10, No. 5, pp. 279-285 (2013).

Lee, et al., Gel Scaffolds of BMP-2-binding Peptide Amphiphile Nanofibers for Spinal Arthrodesis, Adv Healthc Mater, Jan. 7, 2015, 4(1), pp. 131-141.

Liang, et al., "Ectopic osteoinduction and early degradation of recombinant human bone morphogenetic protein-2-loaded porous b-tricalcium phosphate in mice," Biomaterials 26 (2005) 4265-4271.

Lin, et al., "The effect of crosslinking heparin to demineralized bone matrix on mechanical strength and specific binding to human bone morphogenetic protein-2," Biomaterials 29 (2008) 1189-1197.

Luca, et al., "Injectable rhBMP-2-loaded chitosan hydrogel composite: Osteoinduction at ectopic site and in segmental long bone defect," Published online Oct. 26, 2010 in Wiley Online Library (wileyonlinelibrary.com). pp. 66-74.

Luca, et al., "The effects of carrier nature and pH on rhBMP-2-induced ectopic bone formation," Journal of Controlled Release 147 (2010) 38-44.

Ma, et al., "Bone Forming Capacity of Cell- and Growth Factor-Based Constructs at Different Ectopic Implantation Sites," J Biomed Mater Res Part A 2015:103A:439-450.

Ma, et al., "Synergistic effect of RhBMP-2 and bFGF on ectopic osteogenesis in mice," Asian Pacific Journal of Tropical Medicine (2015) 53-59.

Maire, et al., "Bovine BMP osteoinductive potential enhanced by functionalized dextran-derived hydrogels," Biomaterials 26 (2005) pp. 5085-5092.

Matsushita, et al., "A new bone-inducing biodegradable porous 13-tricalcium phosphate," Published online Jun. 25, 2004 in Wiley InterScience, pp. 450-458.

Murata, et al., "Blood Permeability of a Novel Ceramic Scaffold for Bone Morphogenetic Protein-2," Published online Oct. 10, 2016 in WileylnterScience, pp. 469-475.

Murata, et al., "Bone induction in subcutaneous tissue in rats by a newly developed DNA-coated atelocollagen and bone morphogenetic protein," British Journal of Oral and Maxillofacial Surgery (2002) 40, 131-135.

Murata, et al., "Carrier-dependency of cellular differentiation induced by bone morphogenetic protein in ectopic sites," Int. J. Oral Maxillofac. Surg. 1998; 27, 391-396.

Nakamura, et al., "Low dose fibroblast growth factor-2 (FGF-2) enhances bone morphogenetic protein-2 (BMP-2)-induced ectopic bone formation in mice," Bone 36 (2005) 399-407.

Noshi, et al., "Recombinant Human Bone Morphogenetic Protein-2 Potentiates the In Vivo Osteogenic Ability of Marrow/Hydroxyapatite Composites," 2001 International Society for Artificial Organs, 25(3):201-208, Blackwell Science, Inc.

Oreffo, et al., Non Final Office Action dated Feb. 12, 2018 for U.S. Appl. No. 15/306,020.

Oreffo, et al.. Notice of Allowance dated Nov. 5, 2018 for U.S. Appl. No. 15/306,020.

Pawar, et al., Surface selective binding of nanoclay particles to polyampholyte protein chains, The Journal of Chemical Physics 131 045103, 2009.

Pelaez, et al., Effect of rhBMP-2 dose on bone formation/maturation in a rat critical-size calvarial defect model, Journal of Clinical Periodontology, 2014, vol. 41, pp. 827-836.

Poldervaart, et al., "Sustained Release of BMP-2 in Bioprinted Alginate for Osteogenicity in Mice and Rats," PLOS ONE, Aug. 2013, vol. 8, Issue 8, pp. 1-9.

Preativatanyou, et al., "RhBMP-2 and -7 combined with absorbable collagen sponge carrier enhance ectopic bone formation: An in vivo bioassay," Asian Biomedicine vol. 5 No. 1 Feb. 2011; 85-92.

Rajaee, et al., Spinal Fusion in the United States: Analysis of Trends From 1998 to 2008, Spine vol. 37, No. 1, 2012, pp. 67-76.

Ratanavaraporn, et al., "Enhanced osteogenic activity of bone morphogenetic protein-2 by 2-O-desulfated heparin," Acta Biomaterialia 8 (2012) 173-182.

Saito, et al., "A biodegradable polymer as a cytokine delivery system for inducing bone formation," Nature Publishing Group, vol. 19, Apr. 2001, pp. 332-335.

Shi, et al., "The osteogenesis of bacterial cellulose scaffold loaded with bone morphogenetic protein-2," Biomaterials 33 (2012) 6644-6649.

Shields, et al., Adverse Effects Associated with High-Dose Recombinant Human Bone Morphogenetic Protein-2 Use in Anterior Cervical Spine Fusion, 2006, Spine vol. 31, No. 5, pp. 542-547.

Simmons, et al., "Dual growth factor delivery and controlled scaffold degradation enhance in vivo bone formation by transplanted bone marrow stromal cells," Bone 35 (2004) pp. 562-569.

Sotome, et al., "Synthesis and in vivo evaluation of a novel hydroxyapatite/collagen-alginate as a bone filler and a drug delivery carrier of bone morphogenetic protein," Materials Science and Engineering C 24 (2004) pp. 341-347.

Stenfelt, et al., "Pre-incubation of chemically crosslinked hyaluronan-based hydrogels, loaded with BMP-2 and hydroxyapatite, and its effect an ectopic bone formation," J Mater Sci: Mater Med (2014) 25:1013-1023.

Tazaki, et al., "The Effect of Partial Dissolution-Precipitation Treatment on Calcium Phosphate Ceramics in the Release of BMP-2 and

(56) References Cited

OTHER PUBLICATIONS

Osteoinduction," Biomaterials, Institute for Frontier Medical Sciences, Publication, Jun. 10, 2012, pp. 459-468.

Tumialan, et al., The safety and efficacy of anterior cervical discectomy and fusion with polyetheretherketone spacer and recombinant human bone morphogenetic protein-2: a review of 200 patients, J. Neurosurg, Spine, vol. 8, Jun. 2008, pp. 529-535.

Uludag, et al., Characterization of rhBMP-2 pharmacokinetics implanted with biomaterial carriers in the rat ectopic model, Bone Biology and Applications, Genetics Institute, Jan. 1999., pp. 193-202. 2Preclinical Research and Development, Genetics Institute.

Van De Watering, et al., "Non-glycosylated BMP-2 can induce ectopic bone formation at lower concentrations compared to glycosylated BMP-2," Journal of Controlled Release 159 (2012) 69-77.

Vehof, et al., "Ectopic Bone Formation 1n Titanium Mesh Loaded with Bone Morphogenetic Protein and Coated with Calcium Phosphate," Received for publication Feb. 1, 2000, vol. 108, No. 2, pp. 434-443.

Visser, et al., "The effect of an rhBMP-2 absorbable collagen sponge-targeted system on bone formation in vivo." Biomaterials 30 (2009) 2032-2037.

Wang, et al., Preparation of Laponite Bioceramics for Potential Bone Tissue Engineering Applications, PLOS One, Jun. 2014, vol. 9, Issue 6, e99585.

Wang, et al., Recombinant human bone morphogenetic protein induces bone formation, Biochemistry, Proc. Natl, Acad. Sci. USA, vol. 87, Mar. 1990, pp. 2220-2224.

Whang, et al., "Ectopic bone formation via rhBMP-2 delivery from porous bioabsorbable polymer scaffolds," 1998 John Wiley & Sons, Inc. pp. 491-499.

Wijdicks, et al., "Ultrasound Enhances Recombinant Human BMP-2 Induced Ectopic Bone Formation in a Rat Model," Ultrasound in Med. & Biol., vol. 35, No. 10, pp. 1629-1637, 2009.

Wu, et al., "Enhanced healing of rabbit segmental radius defects with surface-coated calcium phosphate cement/bone morphogenetic protein 2 scaffolds," Materials Science and Engineering C 44 (2014) 326-335.

Yamamoto, et al., "Controlled release by biodegradable hydrogels enhances the ectopic bone formation of bone morphogenetic protein," Biomaterials 24 (2003) pp. 4375-4383.

Yang, et al., "Injectable and redox-responsive hydrogel with adaptive degradation rate for bone regeneration," J. Mater. Chem. B, 2014, 2, 295-304.

Yang, et al.. Direct "Click" Synthesis of Hybrid Biphosphonate-Hyaluronic Acid Hydrogel in Aqueous Solution for Biomineralization, Chemistry of Materials, vol. 24, No. 9, May 8, 2012, pp. 1690-1697.

Younger, et al., Morbidity at Bone Graft Donor Sites, Reprinted from Journal of Orthopaedic Trauma, vol. 3, No. 3, 1989 Raven Press, Ltd., NY, pp. 192-195.

Yuasa, et al., "Dexamethasone Enhances Osteogenic Differentiation of Bone Marrow- and Muscle-Derived Stromal Cells and Augments Ectopic Bone Formation Induced by Bone Morphogenetic Protein-2," PLOS ONE, Feb. 6, 2015, 1-23.

Zhang, et al., "Pharmacokinetics and bone formation by BMP-2 entrapped in polyethyleniminecoated albumin nanoparticles," Biomaterials 30 (2009) 5143-5155.

Zhao, et al., "Heparin Potentiates the in Vivo Ectopic Bone Formation Induced by Bone Morphogenetic Protein-2*," The Journal of Biological Chemistry vol. 281, No. 32, p. 23246-23253, Aug. 11, 2006.

Zhao, et al., "The osteogenic effect of bone morphogenetic protein-2 on the collagen scaffold conjugated with antibodies," Journal of Controlled Release 141 (2010) 30-37.

Zheng, et al., "A Novel BMP2-Coprecipitated, Layer-by-Layer Assembled Biomimetic Calcium Phosphate Particle: A Biodegradable and Highly Efficient Osteoinducer," Clinical Implant Dentistry and Related Research, vol. 16, No. 5, 2014, pp. 643-654.

Zhou, et al., "Enhanced bioactivity of bone morphogenetic protein-2 with low dose of 2-N, 6-O-sulfated chitosan in vitro and in vivo," Biomaterials 30 (2009) 1715-1724.

* cited by examiner

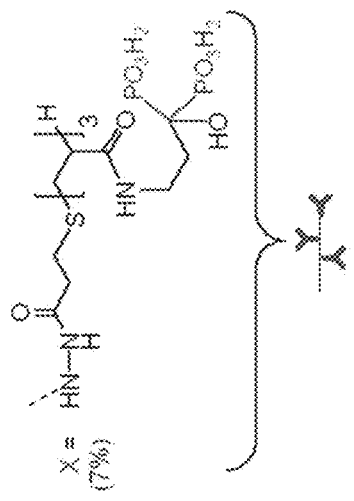
FIG. 1A
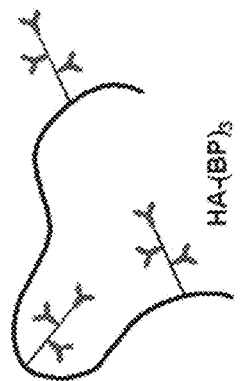
FIG. 1B
FIG. 1D
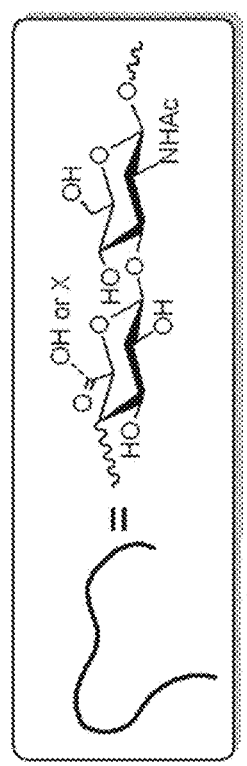
FIG. 1C
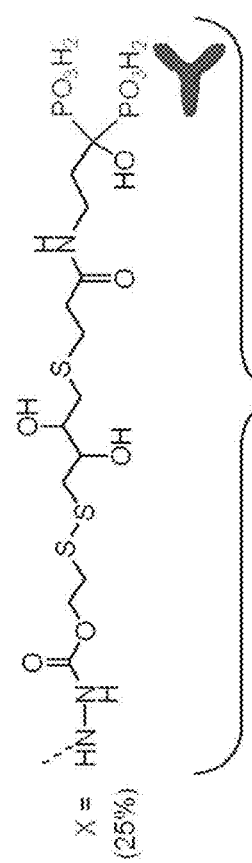
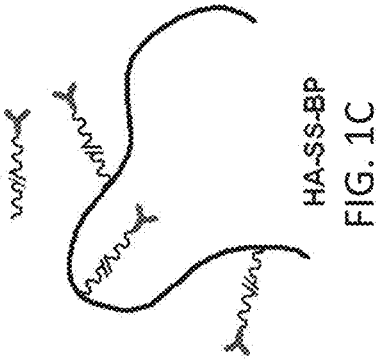

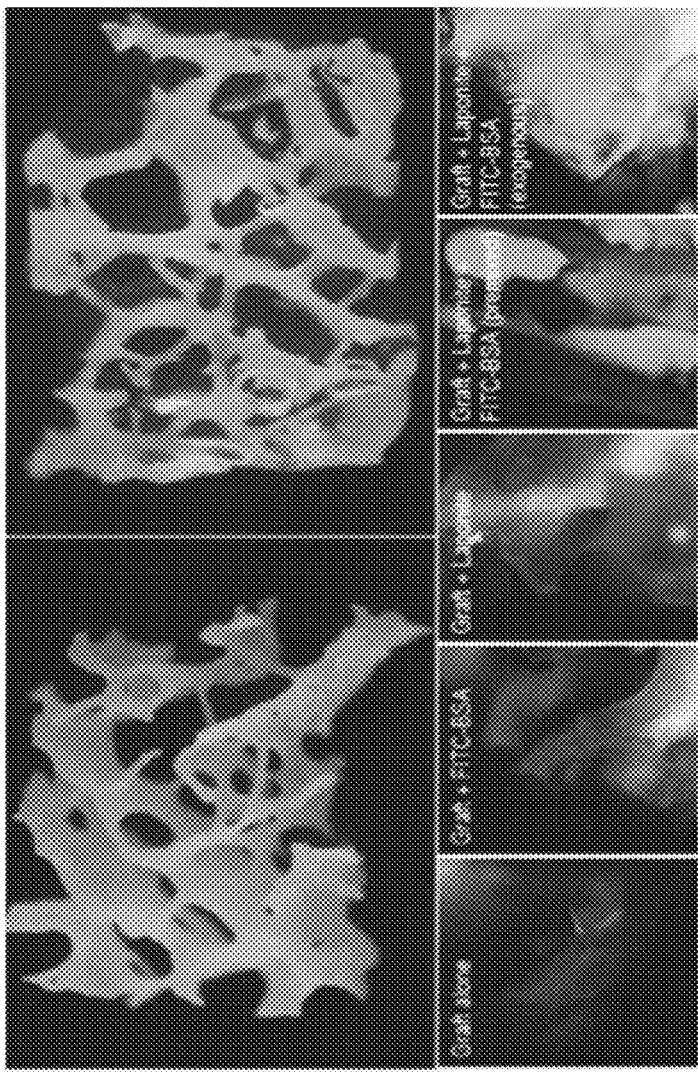
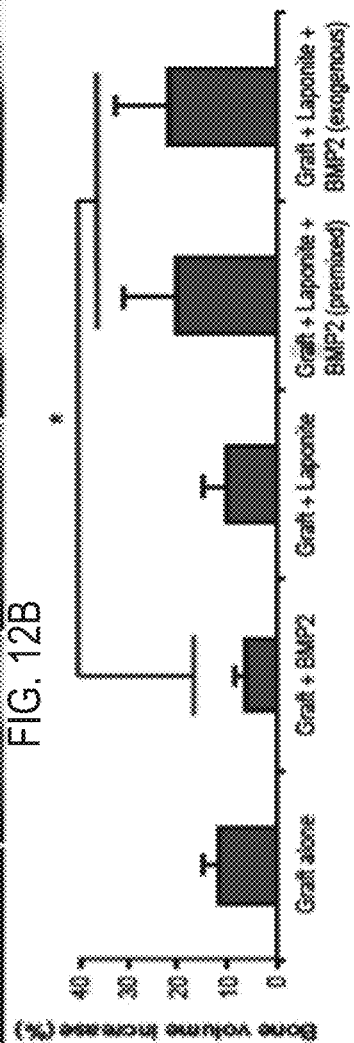
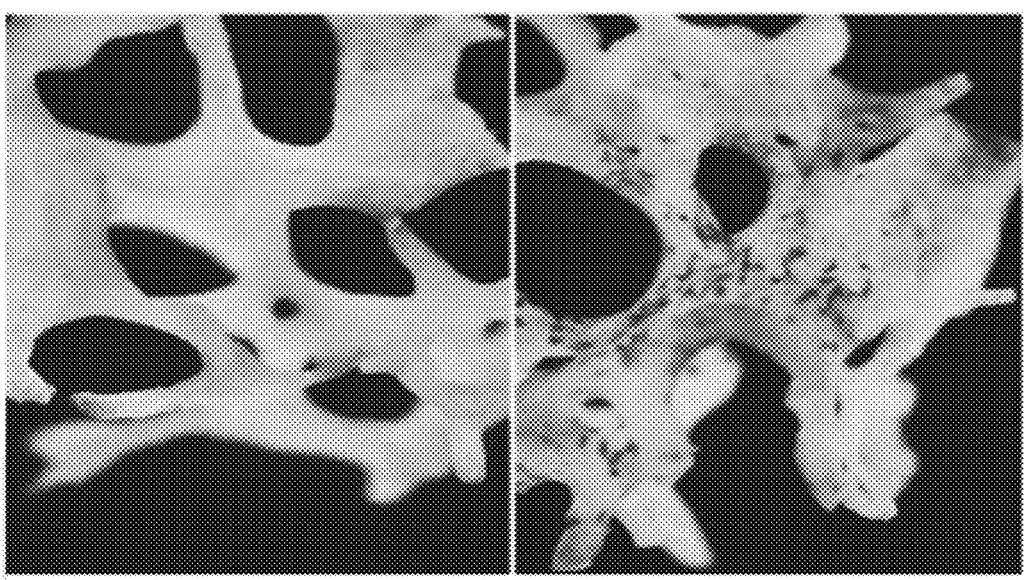
FIG. 12A
FIG. 12B
FIG. 12C

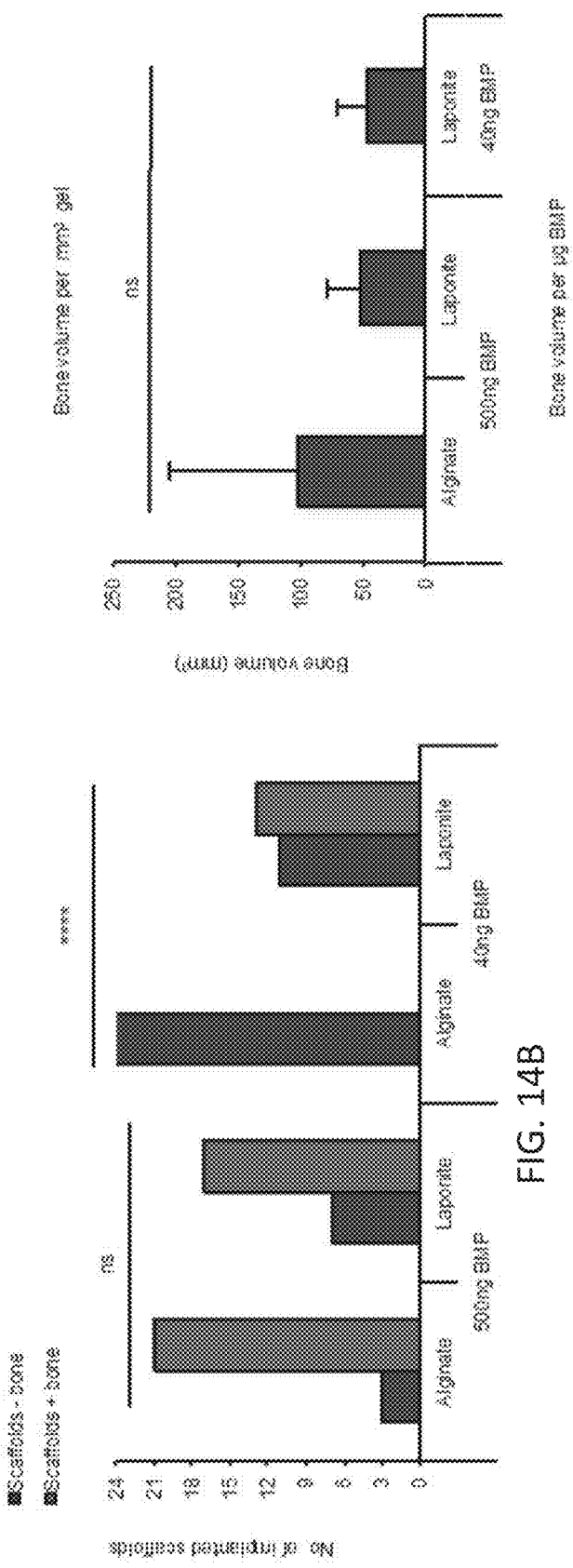
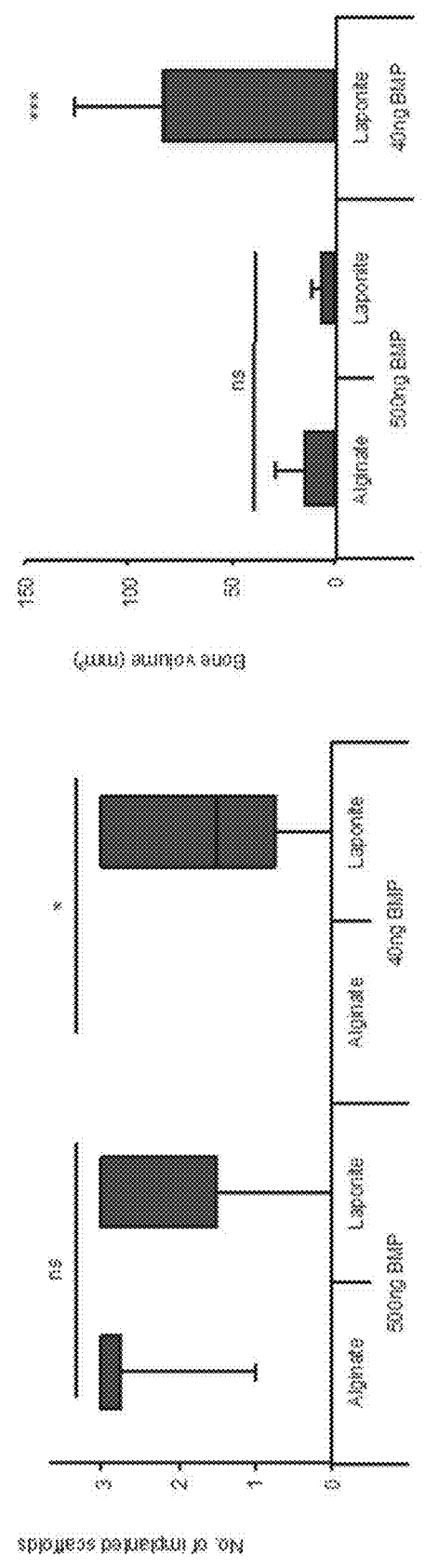
FIG. 14B
FIG. 14C
FIG. 14D

POLYMER-CLAY COMPOSITE AND ORGANOCLAY

This invention relates to polymer-clay composites, hydrogels and organoclays; their methods of manufacture and applications thereof.

Hydrogels are a class of materials abundant in medical devices. They are crosslinked polymer networks that swell but do not dissolve in water. Hydrogels can be made of synthetic polymers like PEG (polyethylene glycol), or natural polymers like hyaluronic acid. Their performance in medical devices can depend on their specific chemistry, which includes but is not limited to the choice of polymer, molecular weight, degree of crosslinking, osmolarity, and concentration of components. Hydrogel-based medical devices can include abdominal adhesion barriers, contact and intraocular lenses, drug-eluting stents, tissue scaffolds, tissue sealants, cosmetic dermal fillers, and encapsulation media.

Hydrogels made from polymer-clay composite have been found to provide some attractive properties. For example, nanoclay particles can serve as multifunctional crosslinkers, producing polymer hydrogels with greater mechanical advantages over conventionally crosslinked hydrogels. Clay based gels have been particularly well suited for providing a regenerative microenvironment in tissue repair (Dawson, J. I. et al. (2011) *Advanced Materials* 23, no. 29: 3304-3308). Nanoclays are nanoparticles of layered mineral silicates that have been used in the pharmaceutical industry as excipients and active agents. Depending on chemical composition and nanoparticle morphology, nanoclays are organized into several classes such as montmorillonite, bentonite, kaolinite, hectorite, and halloysite. Laponite nanoclay is a synthetic layered silicate which is regarded as safe for medical use by the FDA.

Despite the mechanical advantages of nanoclay-polymer based hydrogels, they are still considered to be too unstable for some applications such as bone repair. Re-enforcement of polymer hydrogel by inclusion of clay nanoparticles typically involves a chemical reaction (polymerization of low molecular weight monomers or macromers). Such a chemical reaction can require unfavourable temperatures, pH, or produce toxic side products.

Organically-modified nanoclays (organoclays) are a class of hybrid organic-inorganic nanomaterials with potential uses in polymer nanocomposites, as rheological modifiers, gas absorbents and drug delivery carriers. A need exists for improving organoclays, such as improving the anchoring mechanism by which the organic molecules are attached, in order to functionalise nanoclay particles, for example, for drug delivery.

An aim of the present invention is to provide an improved polymer-clay composite.

According to a first aspect of the invention, there is provided a polymer-clay composite material comprising
  clay nanoparticles; and
  a polymer, and
wherein
  (a) the polymer comprises phosphate and/or phosphonate ligands; or
  (b) the polymer-clay composite further comprises linker molecules comprising a phosphate or phosphonate ligand, wherein the linker molecules are arranged to be anchored to the polymer.

The polymer may form a backbone and a plurality of phosphate and/or phosphonate ligands may be branched therefrom.

The phosphate and/or phosphonate ligands may be arranged to associate, such as ionically bond, with the clay nanoparticles in an aqueous environment. The polymer-clay composite material may further comprise water. The polymer-clay composite material may be a hydrogel.

The phosphate and/or phosphonate ligands may be spaced apart along the polymer strand. The spacing may be about 1-10 monomer units of the polymer, such as 1-10 disaccharide units.

It is understood that the term "hydrogel" may comprise highly hydrated, three dimensional networks of small inorganic particles and/or large organic molecules formed by physical or chemical interaction (C. M. Ofner III, C. M. Klech-Gelotte (2002). Gels and Jellies. In: Encyclopedia of Pharmaceutical Technology. Marcel Dekker, New York, 1327-1344.)

The phosphonate ligands may comprise or consist of bisphosphonate. The phosphate ligands and polymer may comprise or consist of the following formula (I):

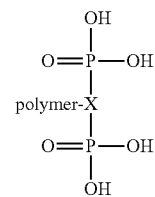

wherein X is $CR^1$, and $R^1$ is H, OH, $NH_2$, $CH_3$, C2-C6 alkane, alkyne, or an aromatic ring; or the following formula (II)

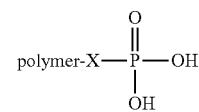

wherein X is O, $NH_2$, $CH_2$, =CH, C2-C6 alkane, alkyne, or an aromatic ring; or a combination thereof.

The invention advantageously provides a robust material for a hydrogel that maintains strong mechanical integrity without any chemical cross-linking, but through physical interactions between clay nanoparticles (NPs) and phosphonate groups anchored to a polymeric backbone, such as the natural glycosaminoglycan, hyaluronan (HA). The exclusion of chemical reactions in the material preparation makes it environmentally safe and applicable for biomedical applications. A further advantage of this approach is that the nature of the phosphonate interaction with clay nanoparticles preserves the rich cation-exchange capacity of clay nanoparticles for purposes of, for example, drug delivery. Conventional clay-polymer nanocomposite hydrogels typically obstruct cation exchange sites and thus attenuate the cation exchange capacity of clay nano particles.

The phosphate and/or phosphonate ligands, such as bisphosphonate, may be anchored/linked to the polymer by chemical bonding via a linker. The linker may comprise a chemical bond between atoms, such as C—C, C=C, C(O)—NH, C—O, C—Si, or C—S.

Advantageously, these bonds can be characterized by different stability under different environmental conditions. Thus, by inclusion of chemically labile bonds (such as disulphide bond) one can engineer bioresponsive hydrogel materials that can be disassembled upon certain conditions.

(as for example 1000-fold higher concentration of thiols in cellular cytoplasm as compared with extracellular environment). Design of hybrid clay-polymer nanoparticles in which phosphate and/or phosphonate ligands, such as bisphosphonate, are linked to polymers through environmentally labile ligands is advantageous in development of drug delivering vehicles with on-site vehicle's disassembly mechanism or conversion of biologically non-active prodrugs into active drugs.

The linker molecule may be an organic molecule. The linker molecule may be selected from any of the group comprising acrylamide, alkane, alkene, alkyne, alcohol, aldehyde, ketone, amino acid, ester, cycloalkane, sugar, and nucleic acid.

The linker molecule may be arranged to be anchored to the polymer by chemical reaction. The chemical reaction may be spontaneous (i.e. self-catalysed), chemically catalysed or photo-catalysed. The linker molecule may comprise a thiol moiety for linking the linker molecule to the polymer by chemical reaction. The linker molecule may comprise a disulphide linked pyridine for linking the linker molecule to the polymer by chemical reaction. The polymer may comprise a disulphide linked pyridine, or a thiol moiety for linking the polymer to the linker molecule by chemical reaction.

The phosphonate ligands may be anchored to the polymer by covalent bonding. The phosphonate ligands may be anchored to the polymer by a disulphide bond.

A clay nanoparticle is understood to be an inorganic nanoparticle. The clay nanoparticle may comprise or consist of silicate. The silicate may comprise layered silicate. The clay nanoparticles may be synthetic (i.e. not occurring in nature), such as synthetic silicate. In one embodiment the clay nanoparticle is a smectite.

The clay nanoparticle may comprise laponite. The clay nanoparticles may comprise any material selected from the group comprising laponite, montmorillonite, bentonite, kaolinite, hectorite, and halloysite; or combinations thereof.

The clay nanoparticles may have an average size of between about 10 nm and about 800 nm in the longest dimension. The clay nanoparticles may have an average size of between about 10 nm and about 300 nm in the longest dimension. The clay nanoparticles may have an average size of between about 10 nm and about 100 nm in the longest dimension. The clay nanoparticles may have an average size of between about 10 nm and about 50 nm in the longest dimension. The clay nanoparticles may have an average size of between about 20 nm and about 50 nm in the longest dimension. The clay nanoparticles may have an average size of between about 20 nm and about 30 nm in the longest dimension. The clay nanoparticles may have an average size of about 25 nm in the longest dimension.

The clay nanoparticles may have an average thickness (shortest dimension) of between about 0.5 and about 2 nm. The clay nanoparticles may have an average thickness of about 1 nm. The clay nanoparticles may have an average thickness of about 0.92 nm. The thickness of the clay nanoparticles may be determined when dispersed in an aqueous environment.

The clay nanoparticles may have an aspect ratio of at least 1:5. The clay nanoparticles may have an aspect ratio of at least 1:10. The clay nanoparticles may have an aspect ratio of at least 1:20. The clay nanoparticles may have an aspect ratio of at least 1:25. The clay nanoparticles may have an aspect ratio of less than 1:100. The clay nanoparticles may have an aspect ratio of less than 1:50. The clay nanoparticles may have an aspect ratio of less than 1:30. The clay nanoparticles may have an aspect ratio of between 1:10 and 1:100. The clay nanoparticles may have an aspect ratio of between 1:10 and 1:50. The clay nanoparticles may have an aspect ratio of between 1:20 and 1:50. The clay nanoparticles may have an aspect ratio of between 1:15 and 1:40. The clay nanoparticles may have an aspect ratio of between 1:15 and 1:30. The clay nanoparticles may have an aspect ratio of between 1:20 and 1:30.

The clay nanoparticles may have a <3 nm to >15 nm aspect ratio. The clay nanoparticles may have an about 1 nm to about 25 nm aspect ratio.

The polymer clay composite may comprise between about 0.5% and about 4% clay nanoparticles (w/v). The polymer clay composite may comprise between about 0.5% and about 4% clay nanoparticles (w/v). The polymer clay composite may comprise about 2% (w/v) clay nanoparticles.

The polymer clay composite may comprise between about 0.5% and about 4% polymer (w/v). The polymer clay composite may comprise between about 0.5% and about 4% polymer (w/v). The polymer clay composite may comprise about 2% (w/v) polymer.

In one embodiment, the polymer clay composite comprises water. The polymer clay composite may comprise phosphate buffered saline or cell culture media.

The clay nanoparticles and polymer may not be cross-linked by covalent bonding, or may not be arranged to be cross-linked by covalent bonding.

The polymer may be natural or synthetic. The polymer may be biodegradeable. The polymer may be biocompatible.

The polymer may comprise or consist of glycosaminoglycan. The glycosaminoglycan may comprise or consist of hyaluronan (HA). The polymer may comprise or consist of a polymer selected from any of the group comprising polyacrylamide; pectin; alginate; carboxymethylcellulose; methylcellulose; PLGA; PEG; polysaccharide, such as starch, cellulose, chitin, alginate, and hyaluronate; protein, such as collagen, gelatine, casein, albumin; polyvinyl alcohol (PVA); polyvinylpyrrolidone (PVP); polyetheleneglycol (PEG); polylactic acid (PLA); and polyhydroxy acid (PHA), or combinations thereof. The polymer may comprise or consist of a polymer selected from any of the group comprising polyacrylamide; pectin; alginate; carboxymethylcellulose; methylcellulose; PLGA; PEG; polysaccharide, such as starch, cellulose, chitin, alginate, and hyaluronate; protein, such as collagen, gelatine, casein, albumin; polyvinylpyrrolidone (PVP); polyetheleneglycol (PEG); polylactic acid (PLA); and polyhydroxy acid (PHA), or combinations thereof. The polymer may comprise or consist of a polymer selected from any of the group comprising poly ([alpha]-hydroxyacids) including poly (D, L-lactide-co-glycolide) (PLGA), poly D,L-lactic acid (PDLLA), polyethyleneimine (PEI), polylactic or polyglcolic acids, poly-lactide polyglycolide copolymers, and poly-lactide poly-glycolide polyethylene glycol copolymers, polyethylene glycol (PEG), polyesters, poly ([epsilon]-caprolactone), poly (3-hydroxybutyrate), poly (s-caproic acid), poly (p-dioxanone), poly (propylene fumarate), poly (orthoesters), polyol/diketene acetals addition polymers, polyanhydrides, poly (sebacic anhydride) (PSA), poly (carboxybiscarboxyphenoxyphosphazene) (PCPP), poly [bis(p-carboxyphenoxy) methane] (PCPM), poly (amino acids), poly (pseudo amino acids), polyphosphazenes, derivatives of poly [(dichloro) phosphazene], poly [(organo) phosphazenes], polyphosphates, polyethylene glycol polypropylene block co-polymers for example that sold under the trade mark Pluronics™, natural or synthetic polymers such as silk, elastin, chitin, chitosan, fibrin, fibrinogen, polysaccharides (including pectins), alginates, collagen, peptides, polypeptides or proteins, copolymers prepared from the monomers of any of these polymers, random blends of these polymers, any suitable polymer and mixtures or combinations thereof.

The polymer may have a molecular weight of at least 10 kDa. The polymer may have a molecular weight of at least 12 kDa. The polymer may have a molecular weight of at least 15 kDa. The polymer may have a molecular weight of at least 20 kDa. The polymer may have a molecular weight of at least 25 kDa. The polymer may have a molecular weight of at least 50 kDa. The polymer may have a molecular weight of at least 100 kDa. The polymer may have a molecular weight of at least 150 kDa. The polymer may have a molecular weight of between about 10 kDa and about 1000 kDa. The polymer may have a molecular weight of between about 15 kDa and about 1000 kDa. The polymer may have a molecular weight of between about 20 kDa and about 1000 kDa. The polymer may have a molecular weight of between about 50 kDa and about 1000 kDa. The polymer may have a molecular weight of about 150 kDa. The polymer may be hyaluronan with a molecular weight of about 150 kDa.

The polymer-clay composite material may further comprise an active agent. The agent may be a therapeutically, prophylactically or diagnostically active substance. The active agent may be a bioactive substance. The active agent may be selected from the group comprising a drug, pro-drug, peptide, protein, and nucleic acid, or combinations thereof. The active agent may comprise or consist of a biomolecule.

The active agent may be a drug, a cell, signalling molecule, such as a growth factor, or any other suitable active agent. For example, the active agent may comprise amino acids, peptides, proteins, sugars, antibodies, nucleic acid, antibiotics, antimycotics, growth factors, nutrients, enzymes, hormones, steroids, synthetic material, adhesion molecules, colourants/dyes (which may be used for identification), radioisotopes (which may be for X-ray detection and/or monitoring of degradation), and other suitable constituents, or combinations thereof. The active agent may comprise an osteogenic agent.

The active agent may comprise or consist of any of the group comprising epidermal growth factor, platelet derived growth factor, basic fibroblast growth factor, vascular endothelial growth factor, insulin-like growth factor, nerve growth factor, hepatocyte growth factor, transforming growth factors and other bone morphogenic proteins, cytokines including interferons, interleukins, monocyte chemotactic protein-1 (MCP-I), oestrogen, testosterone, kinases, chemokinases, glucose or other sugars, amino acids, calcification factors, dopamine, amine-rich oligopeptides, such as heparin binding domains found in adhesion proteins such as fibronectin and laminin, other amines, tamoxifen, cis-platin, peptides and certain toxoids. Additionally, drugs (including statins and NSAIDs), hormones, enzymes, nutrients or other therapeutic agents or factors or mixtures thereof may be included. The active agent may comprise BMP (bone morphogenic protein), such as BMP2. The active agent may comprise VEGF. The active agent may comprise or consist of any of the group comprising angiopoietin 1, angiopoietin 2, BMP7, erythropoietin, IGF 1, PDGF-AB (or —BB), TGF-α, TGF-β. FGFs; PTHrp, PTH, wnt proteins and other growth regulatory factors; or combinations thereof.

Combinations of active agents may be provided in the polymer-clay composite.

The active agent may be heat sensitive and/or pH sensitive. The active agent may be labile, degraded, inactivated, or denatured at temperatures above at least about 30° C. The active agent may be labile, degraded, inactivated, or denatured at temperatures above at least about 50° C. The active agent may be labile, degraded, inactivated, or denatured at temperatures above at least about 70° C. The active agent may be labile, degraded, inactivated, or denatured at temperatures above at least about 100° C. The active agent may be labile, degraded, inactivated, or denatured at temperatures above at least about 150° C. The active agent may be labile, degraded, inactivated, or denatured at a pH<6. The active agent may be labile, degraded, inactivated, or denatured at a pH>8.

In an embodiment where BMP is provided as an active agent the BMP may be provided at a dose of between about 0.01 µg and about 300 µg. In another embodiment the BMP may be provided in the polymer-clay composite at a dose of between about 0.01 µg and about 150m. In another embodiment the BMP may be provided in the polymer-clay composite at a dose of between about 0.01 µg and about 100m. In another embodiment the BMP may be provided in the polymer-clay composite at a dose of between about 0.01 µg and about 80 µg. In another embodiment the BMP may be provided in the polymer-clay composite at a dose of between about 0.01 µg and about 40 µg. In another embodiment the BMP may be provided in the polymer-clay composite at a dose of between about 0.01 µg and about 30 µg. Alternatively, the BMP may be provided in the polymer-clay composite at a dose of between about 0.02 µg and about 30 µg. Alternatively, the BMP may be provided in the polymer-clay composite at a dose of between about 0.03 µg and about 30 µg. Alternatively, the BMP may be provided in the polymer-clay composite at a dose of between about 0.036 µg and about 30 µg. Alternatively, the BMP may be provided in the polymer-clay composite at a dose of between about 0.01 µg and about 20 µg. Alternatively, the BMP may be provided in the polymer-clay composite at a dose of between about 0.01 µg and about 10 µg. Alternatively, the BMP may be provided in the polymer-clay composite at a dose of between about 0.01 µg and about 5 µg. Alternatively, the BMP may be provided in the polymer-clay composite at a dose of between about 0.01 µg and about 1 µg. Alternatively, the BMP may be provided in the polymer-clay composite at a dose of between about 0.01 µg and about 0.1 µg. The lower dose of the above ranges may alternatively be about 0.03 µg. The lower dose of the above ranges may alternatively be about 0.036 µg. The BMP may be provided in the polymer-clay composite at a dose of less than about 30 µg. Alternatively, the BMP may be provided in the polymer-clay composite at a dose of less than about 10 µg. Alternatively, the BMP may be provided in the polymer-clay composite at a dose of less than about 1 µg. Alternatively, the BMP may be provided in the polymer-clay composite at a dose of less than about 0.5 µg. The BMP may be provided in the polymer-clay composite at a dose of at least about 0.03 µg. The BMP may be provided in the polymer-clay composite at a dose of about 0.036 µg.

The skilled person will understand that the dose may be dependent on the clinical context, such as the defect size or the polymer-clay composite implant size. Therefore, in one embodiment the BMP may be provided in the polymer-clay composite at a dose of about 5 µg per $cm^3$ of defect or implant. The BMP may be provided in the polymer-clay composite at a dose of less than about 5 µg per $cm^3$ of defect or implant. The BMP may be provided in the polymer-clay composite at a dose of less than about 2 µg per $cm^3$ of defect or implant. The BMP may be provided in the polymer-clay composite at a dose of less than about 1 µg per $cm^3$ of defect or implant. The BMP may be provided in the polymer-clay composite at a dose of less than about 0.8 µg per $cm^3$ of defect or implant. In another embodiment, the BMP may be provided in the polymer-clay composite at a dose of between about 0.1 and about 5 µg and per $cm^3$ of defect or implant. In another embodiment, the BMP may be provided in the polymer-clay composite at a dose of between about 0.3 and about 5 µg and per $cm^3$ of defect or implant. In another embodiment, the BMP may be provided in the polymer-clay composite at a dose of between about 0.5 and about 5 µg and per $cm^3$ of defect or implant. In another embodiment, the BMP may be provided in the polymer-clay composite at a dose of between about 0.57 and about 5 µg and per $cm^3$ of defect or implant. In another embodiment, the BMP may be provided in the polymer-clay composite at a dose of between about 0.1 and about 1 µg and per $cm^3$ of defect or implant. In another embodiment, the BMP may be provided in the polymer-clay composite at a dose of between about 0.5 and about 3 µg and per $cm^3$ of defect or implant. In another embodiment, the BMP may be provided in the polymer-clay composite at a dose of between about 0.5 and about 2 µg and per $cm^3$ of defect or implant. In another embodiment, the BMP may be provided in the polymer-clay composite at a dose of between about 0.5 and about 1 µg and per $cm^3$ of defect or implant.

The polymer-clay composite material may further comprise a cell. The cell may be a live cell. It is possible to use any animal cell with the composition of the invention. Examples of cells which may be used include bone, osteoprogenitor cells, cartilage, muscle, liver, kidney, skin, endothelial, gut, intestinal, cardiovascular, cardiomycotes, chondrocyte, pulmonary, placental, amnionic, chorionic, foetal or stem cells. Where stem cells are used, they may be non-embryonic stem cells.

The active agent or cells may be added to the polymer-clay composite material during preparation (e.g. pre-mixing in solution prior to forming the material, such as a gel). Alternatively, active agent or cells may be added to the polymer-clay composite material after formation (e.g. exogenously), for example by injection. For example the active agent and/or cells may be provided by injection in a carrier solution, such as saline, at the site of the polymer-clay composite material.

Advantageously, the polymer-clay composite material can cross-link without excess heat, pH, or require other chemical agents for crosslinking that could potentially harm or kill cells. For example, this could allow in situ delivery of hydrogel scaffold and cells for bone repair by pre-seeding cells into the polymer-clay composite material and injecting the polymer-composite material into the repair site, which would then swell to form the hydrogel in situ, whilst conserving the cells or other active agents provided.

The polymer-clay composite material may be a liquid capable of setting into a hydrogel. The polymer-clay composite material may be provided in the form of a hydrogel. The polymer-clay composite material may form a hydrogel upon setting. The polymer-clay composite material may be arranged to set into a hydrogel in an aqueous environment. The polymer-clay composite material may be injectable prior to setting. The hydrogel may form in situ. The polymer-clay composite material may be arranged to set into a hydrogel after exposure to light, such as UV light.

The setting into a hydrogel may be within 10 seconds from mixing the clay nanoparticles with the polymer in an aqueous environment. The setting into a hydrogel may be within 30 seconds from mixing the clay nanoparticles with the polymer in an aqueous environment. The setting into a hydrogel may be within 1 minute from mixing the clay nanoparticles with the polymer in an aqueous environment. The setting into a hydrogel may be within 3 minutes from mixing the clay nanoparticles with the polymer in an aqueous environment. The setting into a hydrogel may be within 4 minutes from mixing the clay nanoparticles with the polymer in an aqueous environment. The setting into a hydrogel may be within 5 minutes from mixing the clay nanoparticles with the polymer in an aqueous environment. The setting into a hydrogel may be within about 6, 7, 8, 9, 10, 15, 20, 30, or 60 minutes from mixing the clay nanoparticles with the polymer in an aqueous environment.

The polymer-clay composite may have, or be arranged to have, a shear modulus of at least about 100 G' Pa after setting into a hydrogel. The polymer-clay composite may have, or be arranged to have, a shear modulus of at least about 200 G' Pa after setting into a hydrogel. The polymer-clay composite may have, or be arranged to have, a shear modulus of at least about 500 G' Pa after setting into a hydrogel. The polymer-clay composite may have, or be arranged to have, a shear modulus of at least about 800 G' Pa after setting into a hydrogel. The polymer-clay composite may have, or be arranged to have, a shear modulus of at least about 1000 G' Pa after setting into a hydrogel. The polymer-clay composite may have, or be arranged to have, a shear modulus of at least about 2000 G' Pa after setting into a hydrogel. The polymer-clay composite may have, or be arranged to have, a shear modulus of at least about 3000 G' Pa after setting into a hydrogel. The polymer-clay composite may have, or be arranged to have, a shear modulus of at least about 4000 G' Pa after setting into a hydrogel. Such shear modulus values may be maintained for at least 24 hours after forming the hydrogel. Such shear modulus values may be maintained for at least 3 days after forming the hydrogel.

The polymer-clay composite may have, or be arranged to have, a loss modulus of at least about 20 G" Pa after setting into a hydrogel. The polymer-clay composite may have, or be arranged to have, a loss modulus of at least about 50 G" Pa after setting into a hydrogel. The polymer-clay composite may have, or be arranged to have, a loss modulus of at least about 100 G" Pa after setting into a hydrogel. The polymer-clay composite may have, or be arranged to have, a loss modulus of at least about 200 G" Pa after setting into a hydrogel. The polymer-clay composite may have, or be arranged to have, a loss modulus of at least about 500 G" Pa after setting into a hydrogel. The polymer-clay composite may have, or be arranged to have, a loss modulus of at least about 800 G" Pa after setting into a hydrogel. The polymer-clay composite may have, or be arranged to have, a loss modulus of at least about 1000 G" Pa after setting into a hydrogel. The polymer-clay composite may have, or be arranged to have, a loss modulus of at least about 2000 G" Pa after setting into a hydrogel. The polymer-clay composite may have, or be arranged to have, a loss modulus of at least about 3000 G" Pa after setting into a hydrogel. The polymer-clay composite may have, or be arranged to have, a loss modulus of at least about 4000 G" Pa after setting into a hydrogel. The polymer-clay composite may have, or be arranged to have, a loss modulus of between about 20 G" Pa and about 1000 G" Pa after setting into a hydrogel. Such loss modulus values may be maintained for at least 24 hours after forming the hydrogel. Such loss modulus values may be maintained for at least 3 days after forming the hydrogel.

The mechanical properties of wet hydrogels may be characterized by rheology (AR200 advanced Rheometer, TA Instruments).

The polymer and clay nanoparticles of the polymer-clay composite material may not be capable of chemically reacting with each other. Where the polymer cross-links, or is arranged to cross-link, with the clay nanoparticles, the cross-linking may not use cation exchange sites of the clay nanoparticles.

Advantageously, the cation-exchange capacity of clay nanoparticles is preserved in the cross-linking to for the hydrogel. This can provide capacity for functional use of the clay nanoparticles in the hydrogel, for example to provide slow release of active agents such as drugs or growth factors. An additional example is the slow release or sustained retention of active agents within hydrogel or uptake into the gel network of active agents from an aqueous environment.

The polymer-clay composite material may be biocompatible. The term "biocompatible" is understood to include non-toxic to the human or animal body. To be biocompatible, the polymer-clay composite material may not cause an immune response.

The polymer-clay composite material may be biodegradeable. The term "biodegradeable" is understood to include the ability to breakdown over time in the tissue or body of a human or animal, and/or in the environment. The time for complete degradation may be at least 1 week, at least 1 month, at least 2 months, at least 6 months, or at least 12 months. The time for complete degradation may be no more than 12 months. The time for complete degradation may be no more than 6 months.

The polymer-clay composite material may further comprise an excipient selected from the group consisting of pharmaceutically acceptable salts, polysaccharides, peptides, proteins, amino acids, synthetic polymers, natural polymers, and surfactants.

According to another aspect of the invention, there is provided a kit for forming a polymer-clay composite material comprising
  clay nanoparticles; and
  a polymer, and
wherein
  (a) the polymer comprises phosphate and/or phosphonate ligands; or
  (b) the kit further comprises linker molecules comprising a phosphate or phosphonate ligand, wherein the linker molecules are arranged to be anchored to the polymer.

The kit may further comprise instructions to mix the clay nanoparticles and the polymer.

The clay nanoparticles and polymer may be in the form of separate liquids intended to be mixed together upon use. The clay nanoparticles and polymer may be in the form of a solid, which may be ready for use after the dissolution of the solid in water. The solid may be a mixture of clay nanoparticle and polymer, or separate solids of clay nanoparticle and polymer may be provided.

The kit may further comprise an active agent. The active agent may be provided separately from the clay nanoparticles and/or polymer. The active agent may be provided associated with/bound to polymer and/or clay particles.

The kit may further comprise a cell, such as a live cell. The cell may be provided separately from the clay nanoparticles and/or polymer. The cell may be provided associated with/bound to polymer and/or clay particles.

According to another aspect of the invention, there is provided a hydrogel formed from the polymer-clay composite material of the invention.

According to another aspect of the invention, there is provided a method of manufacturing a hydrogel material comprising:
  mixing the polymer-clay composite material of the invention in water, and
  allowing the polymer-clay composite material to set into a hydrogel.

The mixing and/or setting may be at room temperature. The mixing and/or setting may be at a temperature of about 25° C. The mixing and/or setting may be at a temperature between about 4° C. and about 40° C. The mixing and/or setting may be at a temperature between about 4° C. and about 35° C. The mixing and/or setting may be at a temperature between about 4° C. and about 25° C. The mixing and/or setting may be at a temperature between about 4° C. and about 80° C. The mixing and/or setting may be at a temperature below 80° C. The mixing and/or setting may be at a temperature below 70° C. The mixing and/or setting may be at a temperature below 60° C. The mixing and/or setting may be at a temperature below 50° C. The mixing and/or setting may be at a temperature below 45° C. The mixing and/or setting may be at a temperature below 40° C. The mixing and/or setting may be at a temperature below 30° C. The mixing and/or setting may be at a temperature of about 37° C.

The mixing and/or setting may be at physiological pH. The mixing and/or setting may be at neutral pH. The mixing and/or setting may be at a pH of between about 5 and about 9. The mixing and/or setting may be at a pH of between about 6 and about 8. The mixing and/or setting may be at a pH of between about 6.5 and about 8. The mixing and/or setting may be at a pH of between about 6.8 and about 7.8. The mixing and/or setting may be at a pH of between about 7 and about 7.5.

The mixing and/or setting may not generate side products, such as toxic side products. "Toxic side product" as used herein is understood to be a substance which would inhibit, destabilise or negatively interfere with a biological system, cell, or biological pathway.

Advantageously, the polymer-clay composite material provides a simple two-part gelation with no chemical reaction required to form the hydrogel from the polymer-clay composite material, which leaves no side products that may be toxic or inhibitive.

The method may further comprise the step of encapsulation of active agent. The active agent may be mixed into the polymer-clay composite material before, during or after mixing.

The method may further comprise the step of encapsulation of biomaterial, such as cells. Cells may be seeded into the polymer-clay composite material before, during or after mixing in water. Cells may be seeded into the water before, during or after mixing in the polymer-clay composite material.

Bioactive molecules, such as drugs, pro-drugs, biomolecules, enzyme, proteins, or small molecules may be loaded into a hydrogel of the invention for delivery to cells by hydrogel degradation.

According to another aspect of the invention, there is provided a method of treatment comprising the administration of the polymer-clay composite material or hydrogel according to the invention to a subject, wherein the treatment is for treatment or prevention of a disease, tissue repair or tissue replacement.

The subject may be a mammal. The subject may be human. The subject may have a bone fracture, cavity, disease, or degeneration.

According to another aspect of the invention, there is provided the polymer-clay composite material or hydrogel according to the invention for use in the treatment of a disease, tissue repair or tissue replacement.

The treatment may be bone repair.

According to another aspect of the invention, there is provided the use of the polymer-clay composite material or the hydrogel according to the invention for tissue engineering, tissue repair, tissue support, tissue replacement, cavity filling, or drug delivery.

According to another aspect of the invention, there is provided a cosmetic procedure comprising the administration of the polymer-clay composite material or the hydrogel according to the invention to a subject.

According to another aspect of the invention, there is provided the use of the polymer-clay composite material or the hydrogel according to the invention for a cosmetic procedure. The cosmetic procedure may be soft-tissue reconstruction, breast augmentation or other correctional or cosmetic surgery.

The tissue may be bone tissue. The tissue may be cartilage tissue. The tissue may be selected from any one of the group comprising bone tissue, cartilage, skin tissue, such as dermis or epidermis; mucosal tissue; neuronal tissue; spinal tissue; organ tissue, such as pancreas tissue, or cardiac tissue; and ischeamic tissue; or combinations thereof.

The tissue repair or replacement may be bone repair or replacement. The tissue repair or replacement may be for cartilage repair or replacement. The tissue repair or replacement may be for tissue regeneration for patients of any of the group of diseases or conditions comprising Alzheimer's, Parkinson's, spinal cord injury, type II diabetes, heart failure, angiogenesis, ischeamia, osteoarthritis, chondrodysplasias, burns, and ulcers, such as diabetic ulcers; or combinations thereof.

According to another aspect of the invention, there is provided the use of a phosphonate or phosphate ligand for crosslinking a clay nanoparticle with a polymer; optionally wherein the phosphonate or phosphate ligand is anchored to the polymer.

According to another aspect of the invention, there is provided an organoclay comprising an organic molecule anchored to a clay nanoparticle via a phosphonate or phosphate ligand.

The present invention advantageously provides an organoclay having an improved anchoring mechanism by which the organic molecules are attached, in order to functionalise nanoclay particles, for example, for drug delivery.

The organic molecule may be an active agent. The active agent may be a therapeutically, prophylactically or diagnostically active substance. The active agent may be a bioactive substance. The active agent may be selected from the group comprising a drug, pro-drug, peptide, protein, and nucleic acid, or combinations thereof. The active agent may comprise or consist of a biomolecule. For example, the active agent may comprise amino acids, peptides, proteins, sugars, antibodies, nucleic acid, antibiotics, antimycotics, growth factors, nutrients, enzymes, hormones, steroids, synthetic material, adhesion molecules, colourants/dyes (which may be used for identification), fluorescent molecules, radioisotopes (which may be for X-ray detection and/or monitoring of degradation), and other suitable constituents, or combinations thereof.

According to another aspect of the invention, there is provided a method of manufacturing an organoclay comprising:
  mixing a dispersion of clay nanoparticles with an organic molecule anchored to a phosphonate or phosphate ligand in an aqueous environment.

The organic molecule may be a bioactive molecule. The bioactive molecule may be selected from the group comprising a drug, a pro-drug, a biomolecule, a protein, a peptide, an oligomer, nucleic acid, oligonucleotide, antibody, antibody fragment, mimic or variant, and a small molecule; or combinations thereof.

According to another aspect of the invention, there is provided the use of the organoclay of the invention for drug delivery, imaging, tracking, or reaction catalysis.

Bioactive molecules, such as drugs, pro-drugs, biomolecules, enzyme, proteins, or small molecules may be loaded into the organoclay of the invention for delivery to cells. The bioactive molecules may be anchored to the surface of the organoclay.

Enzymes may be loaded into hydrogels and onto organoclays for retention of their enzymatic activity. If enzyme is strongly associated with the hydrogel material or organoclay and it retains its activity, it may be used in substrate-mediated enzyme prodrug therapy (SMEPT). For SMEPT, an enzyme of non-human origin may be loaded into the hydrogel or onto an organoclay. The hydrogel or organoclay may be implanted locally at the desired site in the body. Prodrugs may be administered for conversion into active drugs. Advantageously this can be achieved locally with precise concentration upon diffusion of prodrugs into the hydrogel.

According to another aspect of the invention, there is provided the use of the organoclay or hydrogel of the invention for retention of active enzyme for substrate-mediated enzyme prodrug therapy.

The active enzyme may be non-human.

According to another aspect of the invention, there is provided a hydrogel functionalised with an organoclay according to the invention, and optionally, wherein the organoclay is linked to polymer of the hydrogel via phosphonate and/or phosphate ligands.

BMP Dosing

According to another aspect of the invention, there is provided a BMP-clay composite material for the promotion of bone growth in a subject comprising
  clay nanoparticles; and
  BMP (Bone Morphogenic Protein).

In one embodiment, the BMP-clay composite is in solution. The solution may comprise water or saline. The BMP-clay composite material may comprise a BMP solution aqueous phase and a clay nanoparticle solid phase.

Advantageously, the present invention has been shown to be particularly useful to control BMP dosing at a bone defect site. In particular the addition of clay nanoparticles to for BMP delivery provides dosing control, such that much lower doses of BMP can be used to encourage bone formation at the defect relative to other BMP dosing methods available to the clinician. Studies have demonstrated significant adverse effects with higher dose BMP use such as: Heterotopic ossification, osteolysis, and swelling. This surprising development of a highly efficient BMP delivery vehicle offers the potential to reduce the effective dose of BMP, facilitating fracture healing and arthrodesis without precipitation of serious adverse effects.

The BMP-clay composite material may comprise between about 1% and about 7% clay nanoparticles (w/v) in a carrier suspension, such as in water or saline. Alternatively, the BMP-clay composite material may comprise between about 1% and about 5% clay nanoparticles (w/v) in a carrier suspension, such as in water or saline. Alternatively, the BMP-clay composite material may comprise between about 2% and about 5% clay nanoparticles (w/v) in a carrier suspension, such as in water or saline. Alternatively, the BMP-clay composite material may comprise between about 2% and about 4% clay nanoparticles (w/v) in a carrier suspension, such as in water or saline. In one embodiment, the BMP-clay composite material may comprise about 2.5% clay nanoparticles (w/v) in a carrier suspension, such as in water or saline.

The BMP-clay composite may further comprise a polymer to form a BMP-dosed polymer-clay composite material. The polymer may be natural or synthetic. The polymer may be biodegradeable. The polymer may be biocompatible. The polymer may comprise or consist of glycosaminoglycan. The glycosaminoglycan may comprise or consist of hyaluronan (HA). The polymer may comprise or consist of a polymer selected from any of the group comprising polyacrylamide; pectin; alginate; carboxymethylcellulose; methylcellulose; PLGA; PEG; polysaccharide, such as starch, cellulose, chitin, alginate, and hyaluronate; protein, such as collagen, gelatine, casein, albumin; polyvinyl alcohol (PVA); polyvinylpyrrolidone (PVP); polyetheleneglycol (PEG); polylactic acid (PLA); and polyhydroxy acid (PHA), or combinations thereof. The polymer may comprise or consist of a polymer selected from any of the group comprising polyacrylamide; pectin; alginate; carboxymethylcellulose; methylcellulose; PLGA; PEG; polysaccharide, such as starch, cellulose, chitin, alginate, and hyaluronate; protein, such as collagen, gelatine, casein, albumin; polyvinylpyrrolidone (PVP); polyetheleneglycol (PEG); polylactic acid (PLA); and polyhydroxy acid (PHA), or combinations thereof. The polymer may comprise or consist of a polymer selected from any of the group comprising poly ([alpha]-hydroxyacids) including poly (D, L-lactide-co-glycolide) (PLGA), poly D,L-lactic acid (PDLLA), polyethyleneimine (PEI), polylactic or polyglcolic acids, poly-lactide polyglycolide copolymers, and poly-lactide poly-glycolide polyethylene glycol copolymers, polyethylene glycol (PEG), polyesters, poly ([epsilon]-caprolactone), poly (3-hydroxybutyrate), poly (s-caproic acid), poly (p-dioxanone), poly (propylene fumarate), poly (orthoesters), polyol/diketene acetals addition polymers, polyanhydrides, poly (sebacic anhydride) (PSA), poly (carboxybiscarboxyphenoxyphosphazene) (PCPP), poly [bis(p-carboxyphenoxy) methane] (PCPM), poly (amino acids), poly (pseudo amino acids), polyphosphazenes, derivatives of poly [(dichloro) phosphazene], poly [(organo) phosphazenes], polyphosphates, polyethylene glycol polypropylene block co-polymers for example that sold under the trade mark Pluronics™, natural or synthetic polymers such as silk, elastin, chitin, chitosan, fibrin, fibrinogen, polysaccharides (including pectins), alginates, collagen, peptides, polypeptides or proteins, copolymers prepared from the monomers of any of these polymers, random blends of these polymers, any suitable polymer and mixtures or combinations thereof. In one embodiment, the polymer comprises alginate and/or collagen.

The polymer may have a molecular weight of at least 10 kDa. The polymer may have a molecular weight of at least 12 kDa. The polymer may have a molecular weight of at least 15 kDa. The polymer may have a molecular weight of at least 20 kDa. The polymer may have a molecular weight of at least 25 kDa. The polymer may have a molecular weight of at least 50 kDa. The polymer may have a molecular weight of at least 100 kDa. The polymer may have a molecular weight of at least 150 kDa. The polymer may have a molecular weight of between about 10 kDa and about 1000 kDa. The polymer may have a molecular weight of between about 15 kDa and about 1000 kDa. The polymer may have a molecular weight of between about 20 kDa and about 1000 kDa. The polymer may have a molecular weight of between about 50 kDa and about 1000 kDa. The polymer may have a molecular weight of about 150 kDa. The polymer may be hyaluronan with a molecular weight of about 150 kDa.

The polymer of the BMP-dosed polymer-clay composite material may comprise phosphate and/or phosphonate ligands, such as bisphosphonate. Alternatively, the BMP-dosed polymer-clay composite material may further comprise linker molecules comprising a phosphate or phosphonate ligand, wherein the linker molecules are arranged to be anchored to the polymer. In one embodiment of the BMP-dosed polymer-clay composite material, the clay nanoparticle comprises laponite and the polymer comprises alginate and/or collagen.

According to another aspect of the invention, there is provided the use of clay nanoparticles in combination with a dose of BMP, for the promotion of bone growth in a subject.

The use of the clay nanoparticles in combination with a dose of BMP may further comprise the use with clay nanoparticles in a polymer.

According to another aspect of the invention, there is provided a method of treatment comprising the administration of the BMP-clay composite material according to the invention to a subject, wherein the treatment is for treatment or prevention of a disease, tissue repair or tissue replacement.

According to another aspect of the invention, there is provided BMP-clay composite material in accordance with the invention for use in the treatment or prevention of a disease, or for use in tissue repair or tissue replacement.

In one embodiment the BMP may be provided in the BMP-clay composite at a dose of between about 0.01 µg and about 300 µg. In another embodiment the BMP may be provided in the BMP-clay composite at a dose of between about 0.01 µg and about 150 µg. In another embodiment the BMP may be provided in the BMP-clay composite at a dose of between about 0.01 µg and about 100 µg. In another embodiment the BMP may be provided in the BMP-clay composite at a dose of between about 0.01 µg and about 80 µg. In another embodiment the BMP may be provided in the BMP-clay composite at a dose of between about 0.01 µg and about 40 µg. In another embodiment the BMP may be provided in the BMP-clay composite at a dose of between about 0.01 µg and about 30 µg. Alternatively, the BMP may be provided in the BMP-clay composite at a dose of between about 0.02 µg and about 30 µg. Alternatively, the BMP may be provided in the BMP-clay composite at a dose of between about 0.03 µg and about 30 µg. Alternatively, the BMP may be provided in the BMP-clay composite at a dose of between about 0.036 µg and about 30 µg. Alternatively, the BMP may be provided in the BMP-clay composite at a dose of between about 0.01 µg and about 20 µg. Alternatively, the BMP may be provided in the BMP-clay composite at a dose of between about 0.01 µg and about 10 µg. Alternatively, the BMP may be provided in the BMP-clay composite at a dose of between about 0.01 µg and about 5 µg. Alternatively, the BMP may be provided in the BMP-clay composite at a dose of between about 0.01 µg and about 1 µg. Alternatively, the BMP may be provided in the BMP-clay composite at a dose of between about 0.01 µg and about 0.1 µg. The lower dose of the above ranges may alternatively be about 0.03 µg. The lower dose of the above ranges may alternatively be about 0.036 µg. The BMP may be provided in the BMP-clay composite at a dose of less than about 30 µg. Alternatively, the BMP may be provided in the BMP-clay composite at a dose of less than about 10 µg. Alternatively, the BMP may be provided in the BMP-clay composite at a dose of less than about 1 µg. Alternatively, the BMP may be provided in the BMP-clay composite at a dose of less than about 0.5 µg. The BMP may be provided in the BMP-clay composite at a dose of at least about 0.03 µg. The BMP may be provided in the BMP-clay composite at a dose of about 0.036 µg.

The skilled person will understand that the dose may be dependent on the clinical context, such as the defect size or the polymer-clay composite implant size. Therefore, in one embodiment the BMP may be provided at a dose of about 5 µg per $cm^3$ of defect or implant. The BMP may be provided at a dose of less than about 5 µg per $cm^3$ of defect or implant. The BMP may be provided at a dose of less than about 2 µg per $cm^3$ of defect or implant. The BMP may be provided at a dose of less than about 1 µg per $cm^3$ of defect or implant. The BMP may be provided at a dose of less than about 0.8 µg per $cm^3$ of defect or implant. In another embodiment, the BMP may be provided at a dose of between about 0.1 and about 5 µg and per $cm^3$ of defect or implant. In another embodiment, the BMP may be provided at a dose of between about 0.3 and about 5 µg and per $cm^3$ of defect or implant. In another embodiment, the BMP may be provided at a dose of between about 0.5 and about 5 µg and per $cm^3$ of defect or implant. In another embodiment, the BMP may be provided at a dose of between about 0.57 and about 5 and per $cm^3$ of defect or implant. In another embodiment, the BMP may be provided at a dose of between about 0.1 and about 1 µg and per $cm^3$ of defect or implant. In another embodiment, the BMP may be provided at a dose of between about 0.5 and about 3 and per $cm^3$ of defect or implant. In another embodiment, the BMP may be provided at a dose of between about 0.5 and about 2 µg and per $cm^3$ of defect or implant. In another embodiment, the BMP may be provided at a dose of between about 0.5 and about 1 and per $cm^3$ of defect or implant.

The BMP may be BMP-2 or BMP-7. The BMP may be selected from any of the group comprising BMP-2, BMP-3, BMP-4, BMP-6, BMP-7 (OP-1), and BMP-8, or combinations thereof. In one embodiment the BMP is BMP-2.

According to another aspect of the invention, there is provided a kit for preparing a BMP-clay composite material for the promotion of bone growth in a subject comprising
 clay nanoparticles as described herein; and
 BMP as described herein.

The kit may further comprise a polymer for provision of a BMP-dosed polymer-clay composite material.

According to another aspect of the invention, there is provided a method of preparing a BMP-clay composite material, such as a BMP-dosed polymer-clay composite material, comprising the steps of:
 mixing BMP and clay nanoparticles in a solution;
 allowing the solution to dry or set into a gel to form the BMP-clay composite material.

According to another aspect of the invention, there is provided a method of preparing a BMP-clay composite material, such as a BMP-dosed polymer-clay composite material, comprising the steps of:
 allowing a clay nanoparticle solution to dry or set into a gel;
 adding a solution of BMP to the clay nanoparticles, to form the BMP-clay composite material.

The clay nanoparticles or the pre-mixed BMP-clay solution may be applied to a bone defect site prior to drying or setting into a gel. For example the BMP-clay solution may be applied to a defect surface and allowed (or encouraged) to dry into a film. The dry BMP-clay film may rehydrate to form a gel, for example in vivo. Alternatively, the gel may be formed prior to use (e.g. ex vivo), then liquidised for injection (for example by shearing), once injected it can be allowed to set into a gel.

The BMP may be mixed in solution with the clay prior to application to a bone defect site. Alternatively the clay nanoparticles may be applied to the bone defect site followed by addition of BMP in solution. In an embodiment where a BMP-dosed polymer-clay composite material is provided, the BMP may be mixed with the polymer-clay solution prior to setting into the polymer-clay composite material, such as a gel (e.g. BMP is pre-mixed into the polymer-clay composite material prior to formation). Alternatively, in an embodiment where a BMP-dosed polymer-clay composite material is provided, the BMP may be added exogenously to the polymer-clay composite material.

The skilled person can determine the preferred BMP addition method as necessary for the appropriate bone growth effect. Advantageously, exogenous addition could allow multiple doses to be delivered via injection, which is still localised through the presence of the polymer-clay composite material at a defect site.

Accordingly, the methods of the invention may comprise further exogenous additions of BMP doses, for example by injection. One, two, three, four, or more additional doses of BMP may be added following the application of the invention.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1A shows a backbone of hyaluronic acid in which part of carboxylate groups are modified with side groups X. These groups are terminated with bisphosphonates.

FIG. 1B shows one of two types of attachment of bisphosphonate groups to hyaluronan polymeric backbone through a labile disulfide linker (HA-SS-BP derivative).

FIG. 1C shows one of two types of attachment of biophosphonate groups to hyaluronan polymeric backbone through a linker containing more stable chemical bonds (HA-$(BP)_3$).

FIG. 1D shows another type of attachment where several BP groups are linked to one attachment site of hyaluronan. The bisphosphonate-modified hyaluronan and clay (laponite) nanoparticles are two essential components that form a polymer-clay nanocomposite hydrogel through harnessing the laponite-bisphosphonate interactions. Specifically, the anionic bisphosphonate groups serve to crosslink to the cationic edges of the clay nanoparticle to form a strong hydrogel.

Figure 2:
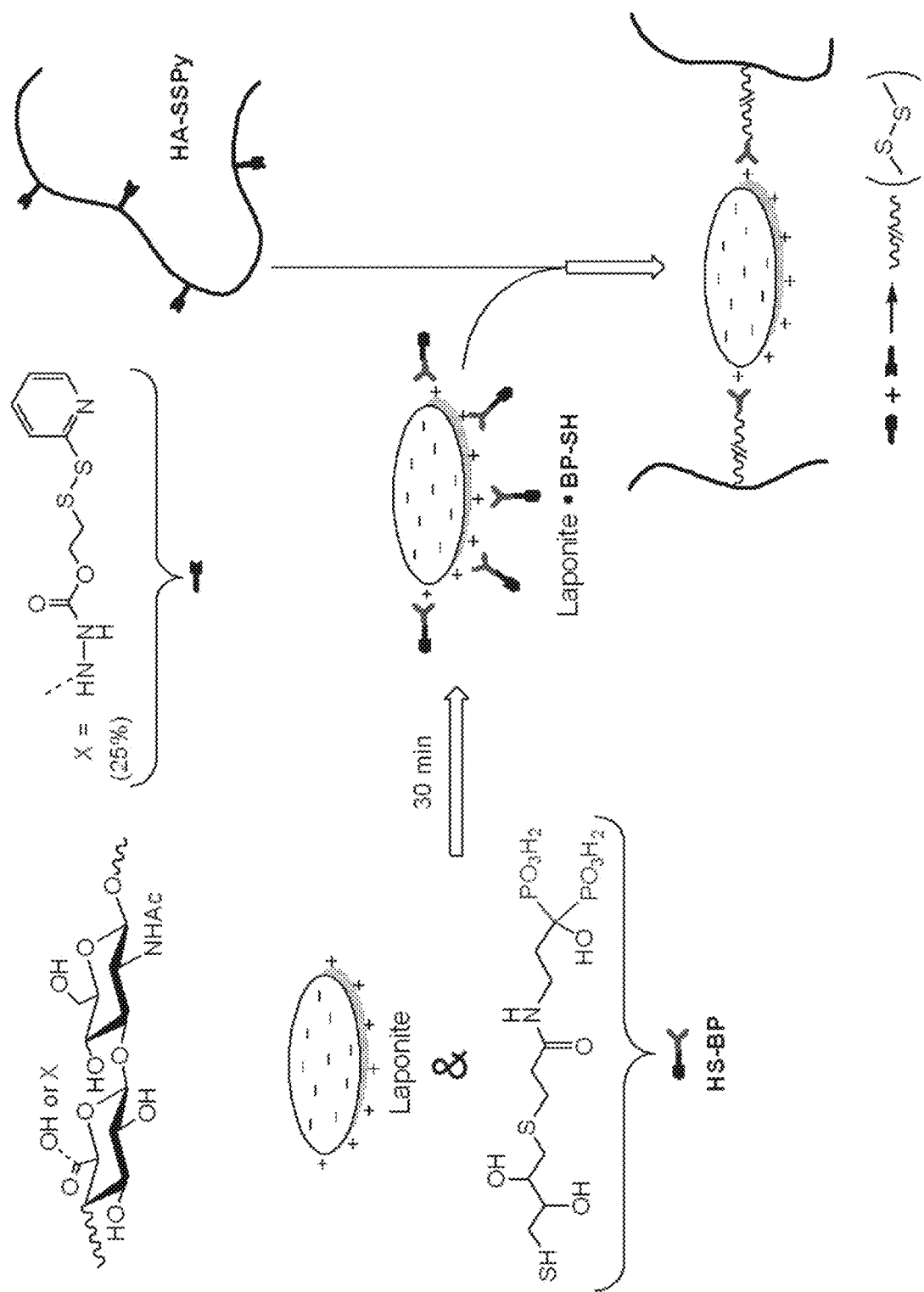

FIG. 2 represents an example of the concept of functionalization of clay nanoparticles with useful functionality X basing on interactions between the nanoparticles and a difunctional BP-X linker. When X is a thiol group, thiol-functionalized nanoparticles can be mixed with pyridyldithio-modified hyaluronan (HA-SSPy) afford a chemically (disulphide) cross-linked hydrogel.

Figure 3:
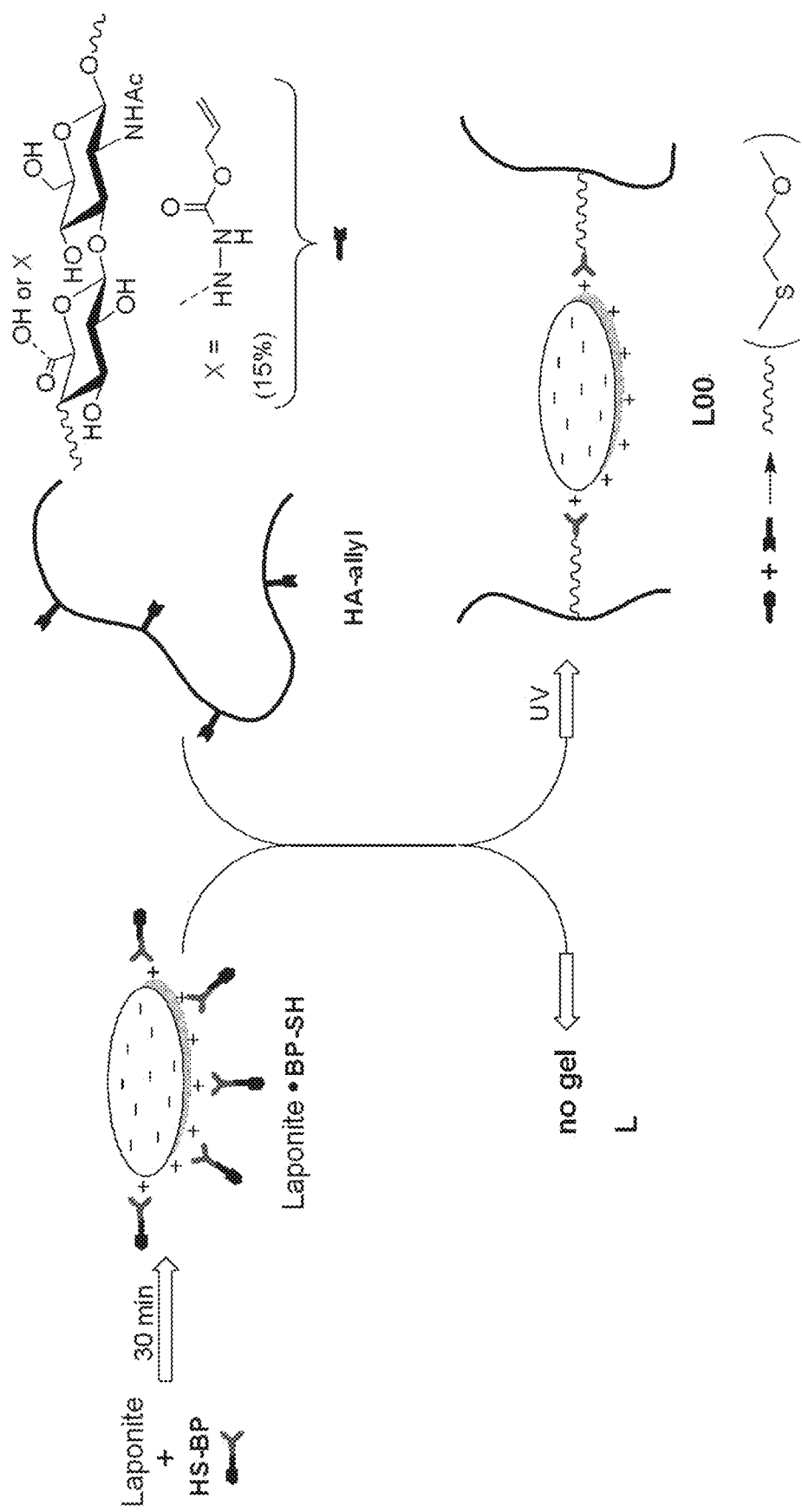
Figure 4B:
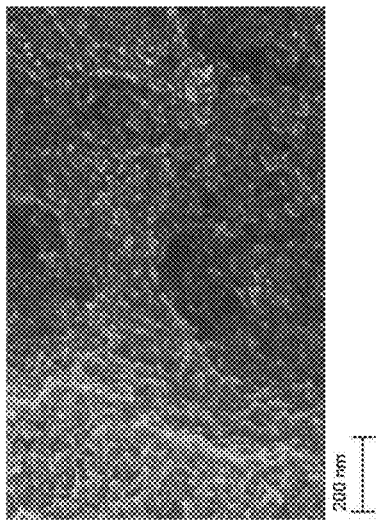
Figure 4D:
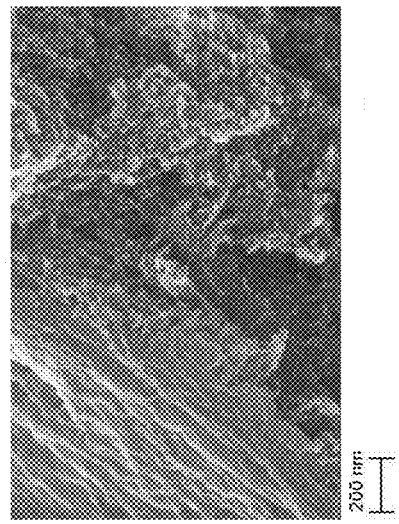
Figure 4A:
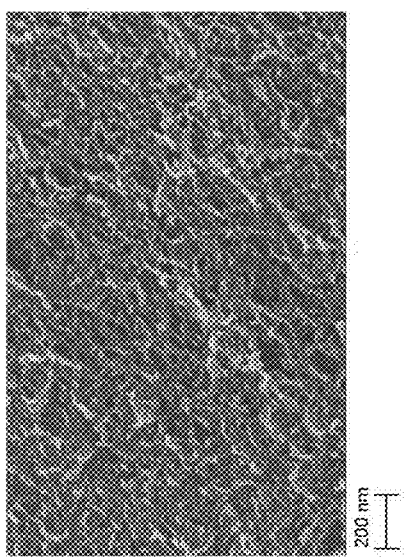
Figure 4C:
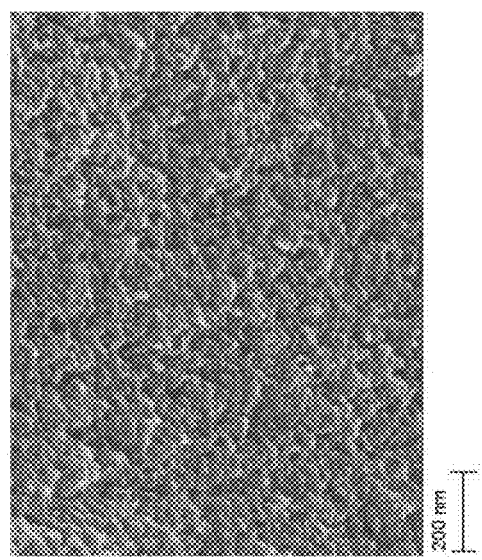

FIG. 3 shows another example of the concept of functionalization of clay nanoparticles with useful functionality X. Specifically, thiol-functionalized nanoparticles (X is a thiol group) participate in a UV-light triggered thiol-ene chemical cross-linking by allyl-modified hyaluronan (HA-allyl) affording a thioether cross-linked hydrogel.

FIGS. 4A-4D show SEM images of different types of physical hyaluronan-bisphosphonate•laponite hydrogels of the invention. L003 corresponds to chemically (disulfide) cross-linked hydrogel formed through mixing of pyridyldithio-modified hyaluronan (HA-SSPy) with the thiol-functionalized Lanonite NPs. L006 corresponds to physically cross-linked hydrogel prepared from HA-(BP)$_3$ derivative and Lanonite NPs. Preparation of L007 and L008 hydrogels was analogous to the preparation of L006 except that either Lanonite NPs (for L007) or HA-(BP)$_3$ (for L008) were pre-treated with sodium pyrophosphate or magnesium chloride respectively.

Figure 5A:
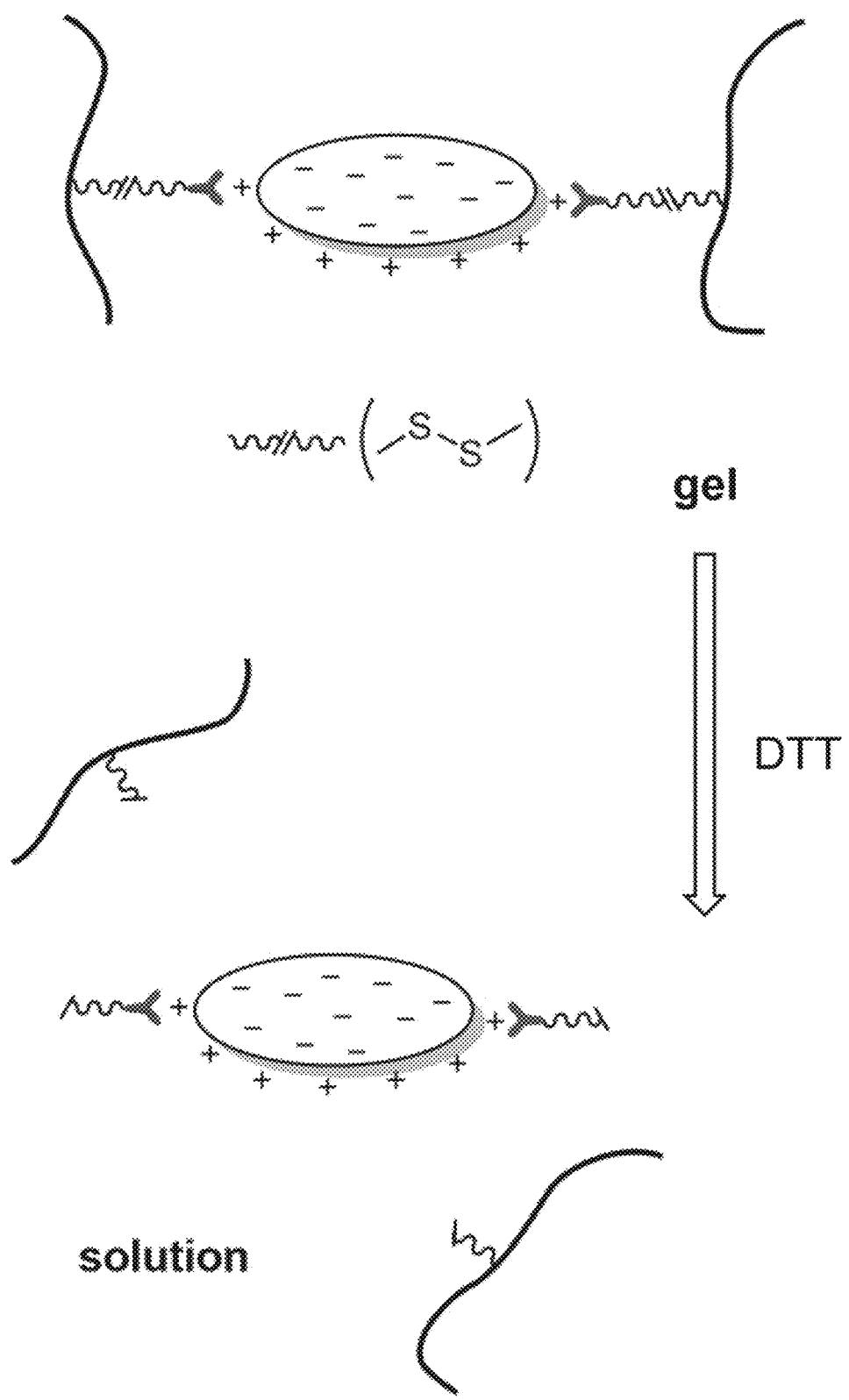

FIG. 5A shows thiol-triggered disassembly of hydrogels containing disulfide labile linkages between BP groups and HA backbone upon action of a reducing agent (such as dithiothreitol, DTT).

Figure 5B:
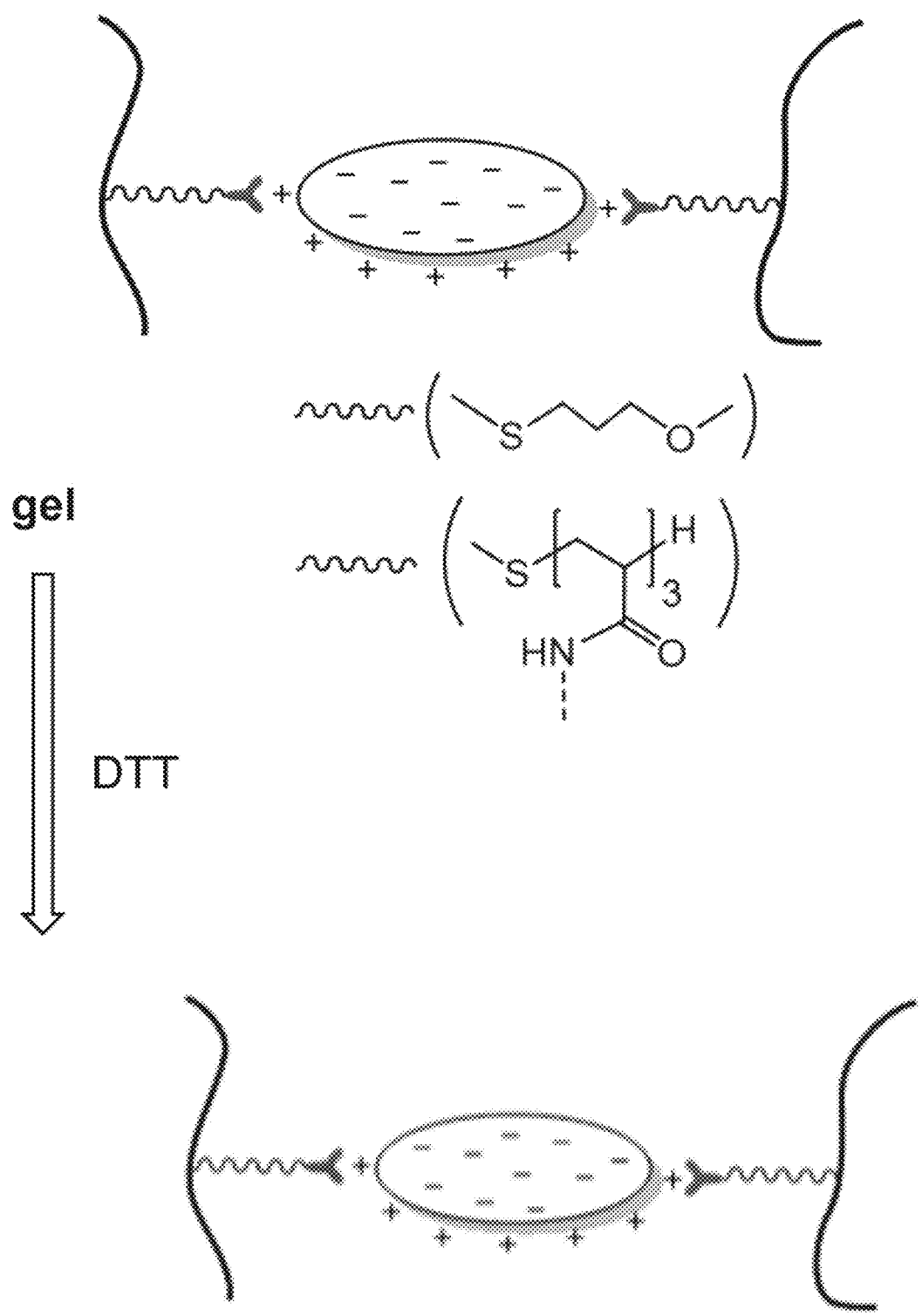

FIG. 5B shows hydrogels containing thioether linkages, which are stable under the treatment illustrated.

Figure 6A:
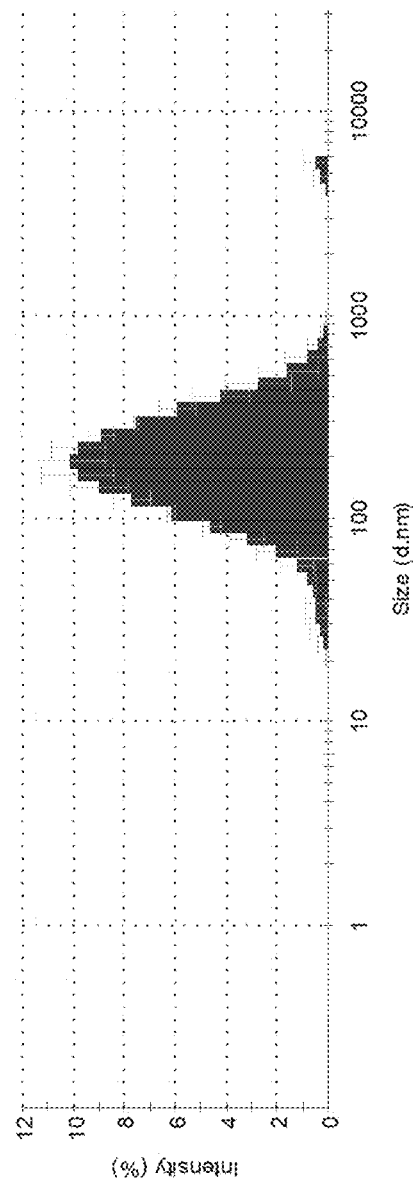
Figure 6B:
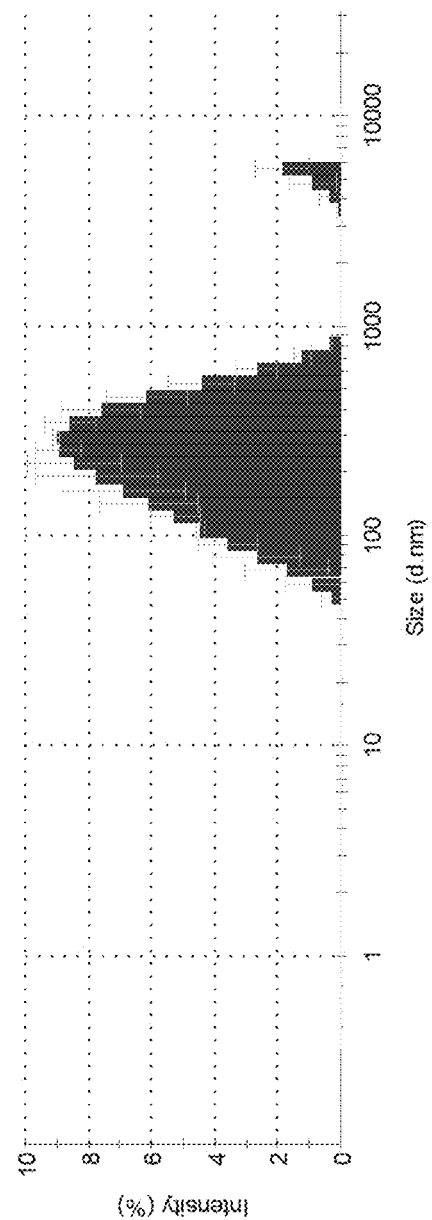
Figure 6C:
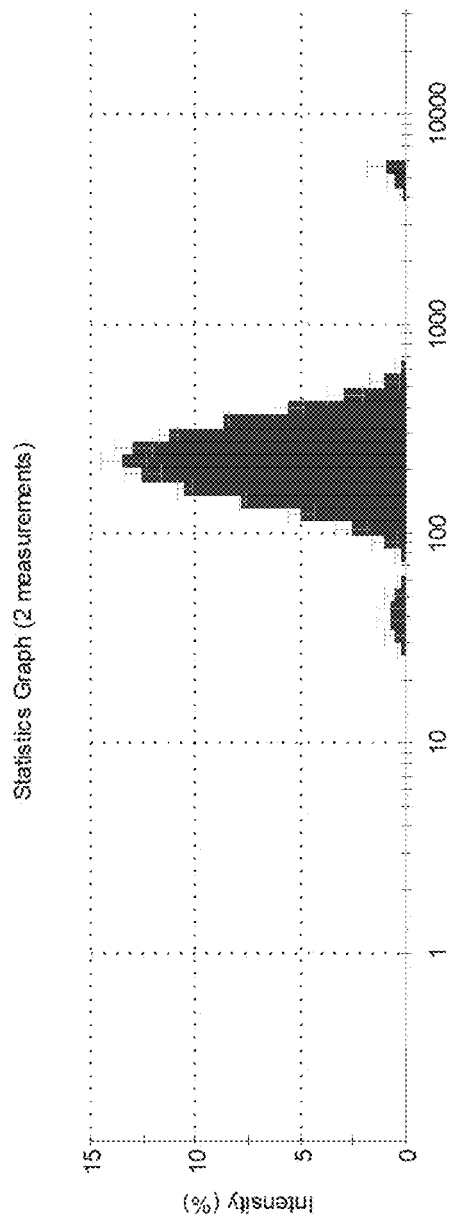
Figure 6D:
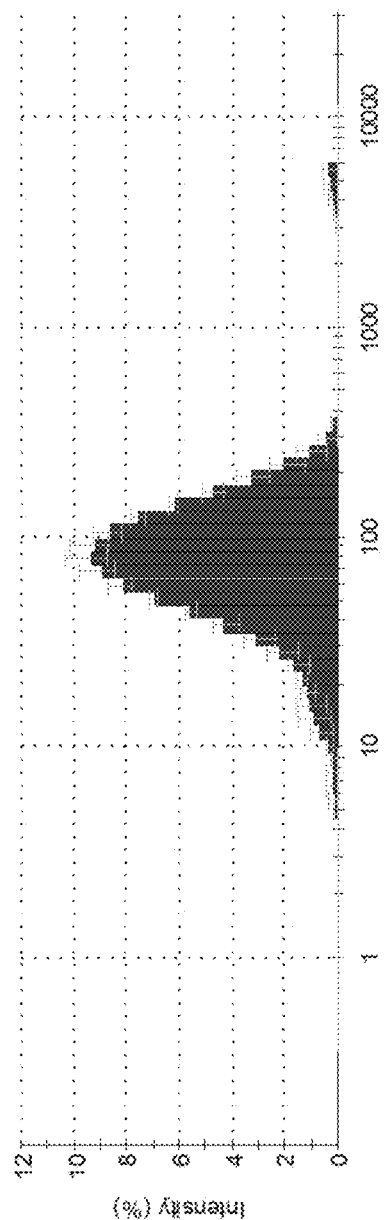
Figure 6E:
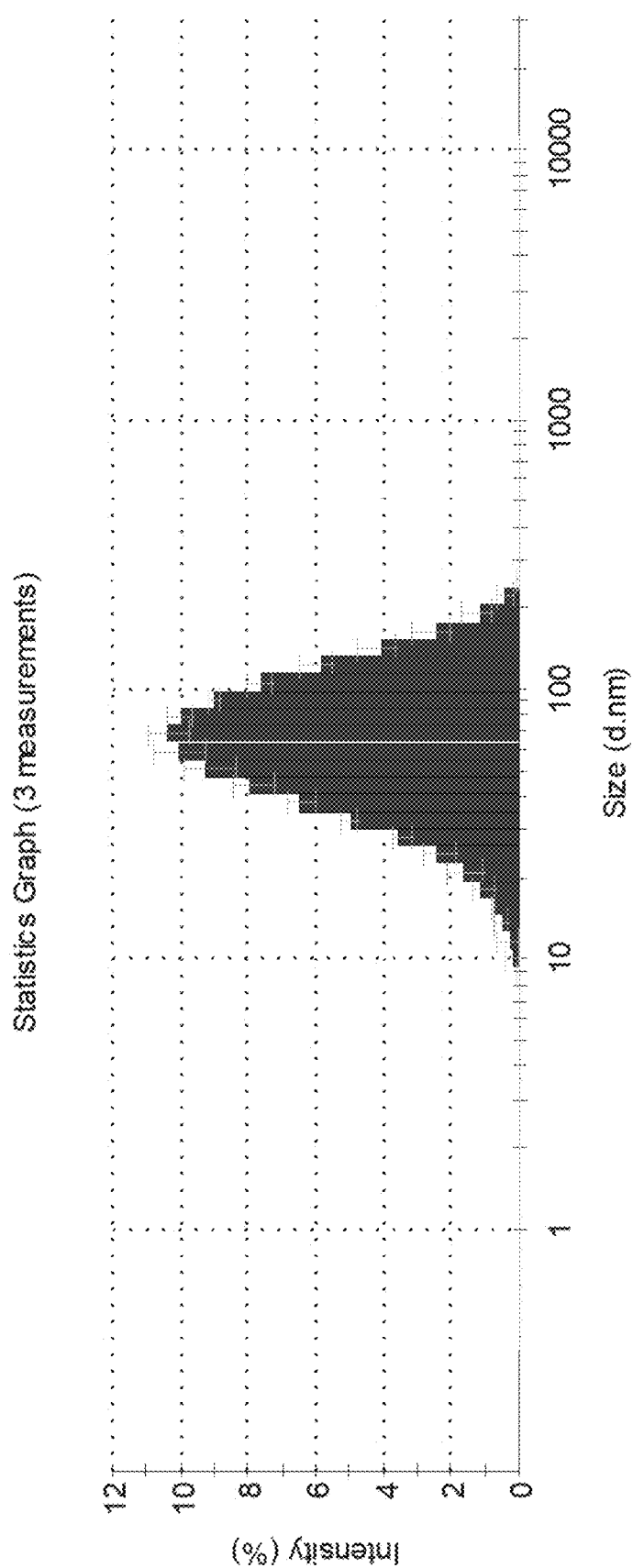

FIGS. 6A-6E show dynamic light scattering (DLS) spectra of nanoparticles obtained after DTT treatment of hydrogel L001 (FIG. 6A), hydrogel L002 (FIG. 6B), and hydrogel L003 (FIG. 6C). For comparison, DLS spectrum of parent Laponite NPs (FIG. 6D) and thiol-functionalized Laponite NPs (FIG. 6E) in water are shown. Hydrogels L001 and L002 were obtained from HA-SS-BP derivative and Lanonite NPs, while hydrogel L003 was obtained chemically between thiol-functionalized Laponite NPs and pyridyldithio-modified hyaluronan (HA-SSPy).

Figure 7:
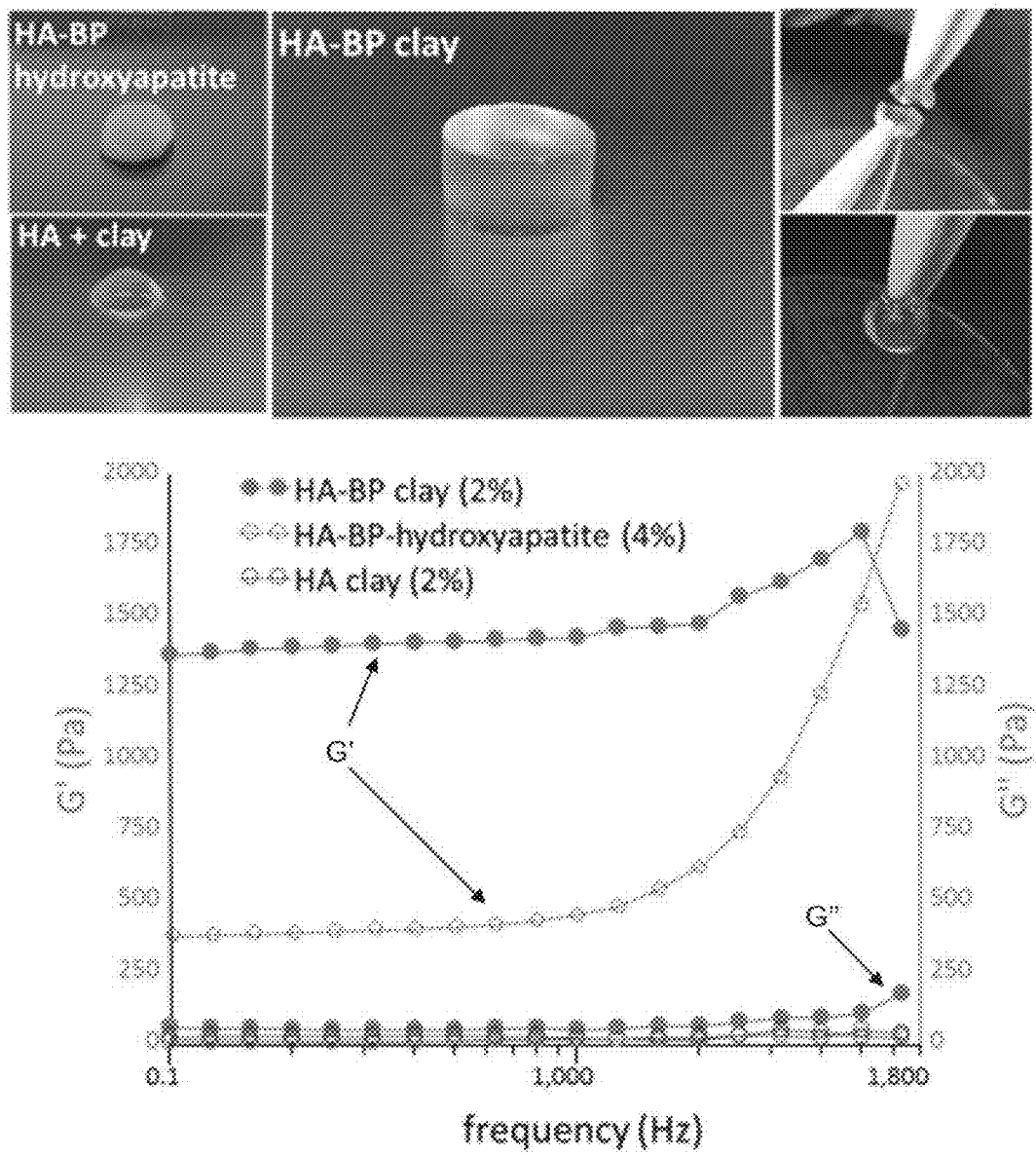

FIG. 7 shows the appearance of natural (non-modified) hyaluronan (left image) and bisphosphonate-modified hyaluronan (middle image) after mixing with a dispersion of laponite nanoparticles. The right image shows that the formed physical hyaluronan-bisphosphonate•Laponite hydrogel possesses self-healing properties. Frequency sweep experiment shows that G' and G" for the mixture of non-modified hyaluronan and Laponite i.e. represents a liquid in a range of frequencies. Oppositely, G' is higher than G" for the mixture of hyaluronan-bisphosphonate and laponite (gel state). The same tendency of physical gel formation was also observed upon interaction of hyaluronan-bisphosphonate with calcium phosphate nanoparticles.

Figure 8A:
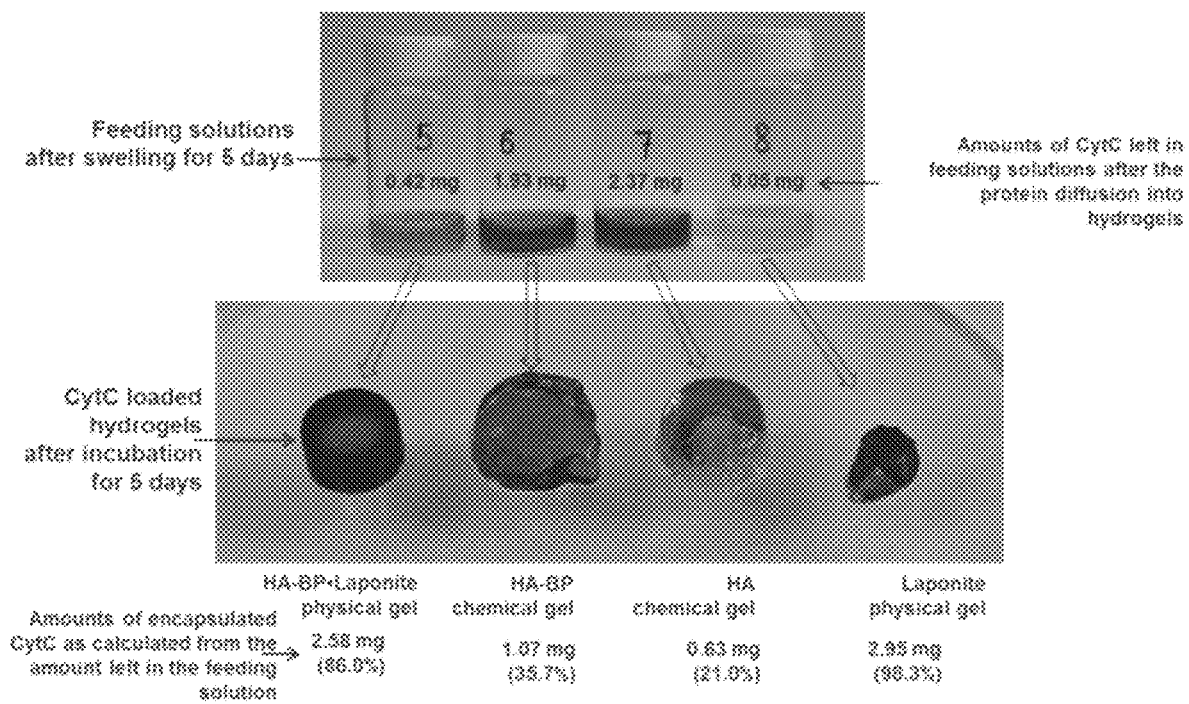
Figure 8B:
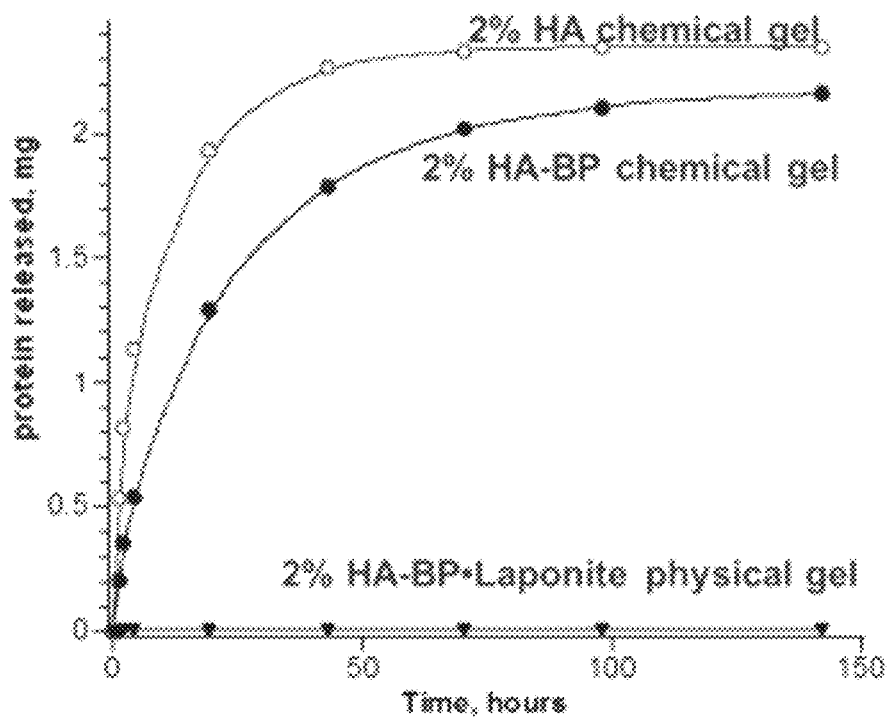

FIGS. 8A-8B show details of loading of different types of hydrogels with a model protein, cytochrome c (cyt c). HA-BP•Laponite physical gel was formed by physical interactions between polymeric hyaluronan-bisphosphonate and Laponite nanoparticles. HA-BP chemical gel was formed as a result of hydrazone cross-linking between polymer chains of aldehyde-modified hyaluronan (HA-al) and hydrazide & bisphosphonate dual-modified hyaluronan (HA-by-BP). Control HA chemical gel was formed as a result of hydrazone cross-linking between polymer chains of HA-al and hydrazide-modified hyaluronan (HA-hy). Control Laponite physical gel was formed from the dispersion of laponite nanoparticles. 0.3 mL hydrogels were incubated in 3 mL of PBS containing 3 mg of the protein for 5 days. FIG. 8A shows images of the protein feeding solutions after loading while the lower panel shows images of the hydrogels after loading. The protein loaded hydrogels were then incubated in pure PBS. FIG. 8B shows the amount of the released cyt c over time.

Figure 9A:
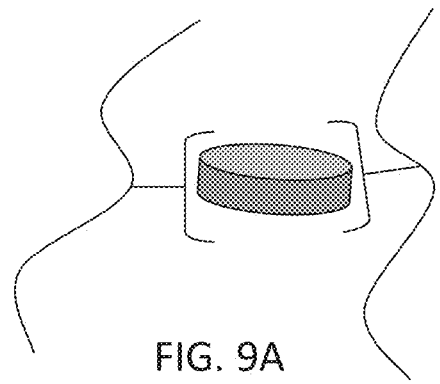
Figure 9B:
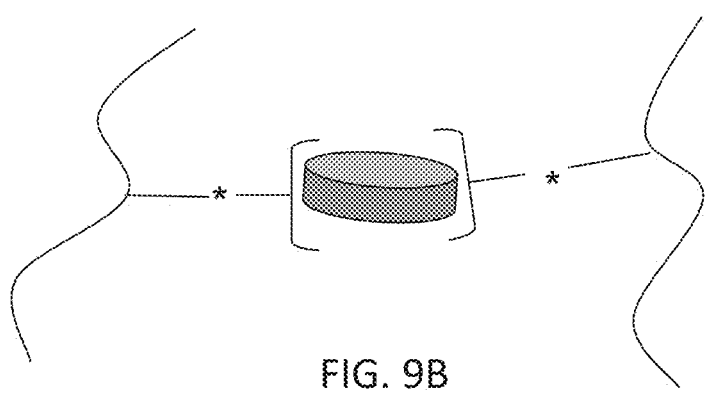
Figure 9C:
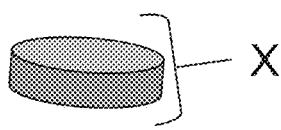
Figure 9D:
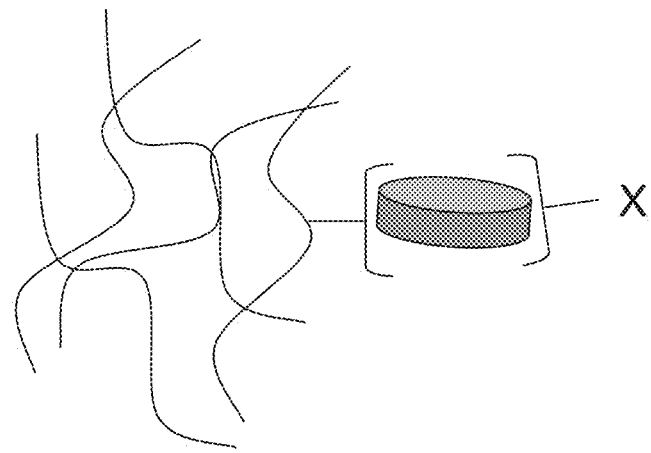

FIGS. 9A-9D provide schematic illustrations of different uses of the invention. In particular, FIG. 9A shows polymer strands linked to each other via a clay nanoparticle interaction with phosphate or phosphonate ligands on the polymer strands. FIG. 9B shows polymer strands linked to each other via a clay particle interaction with phosphate or phosphonate ligands on the polymer strands, wherein * represents a link, such as a disulphide bond between the phosphonate or phosphate ligand and the polymer strand. FIG. 9C shows a functionalised organoclay having active agent X anchored to the clay nanoparticle via a phosphonate or phosphate ligand. FIG. 9D shows a polymer hydrogel functionalised by linking to an organoclay having active agent X anchored to the clay nanoparticle via a phosphonate or phosphate ligand. The clay nanoparticle may or may not be linked to the polymer via phosphate or phosphonate ligand.

Figure 10A:
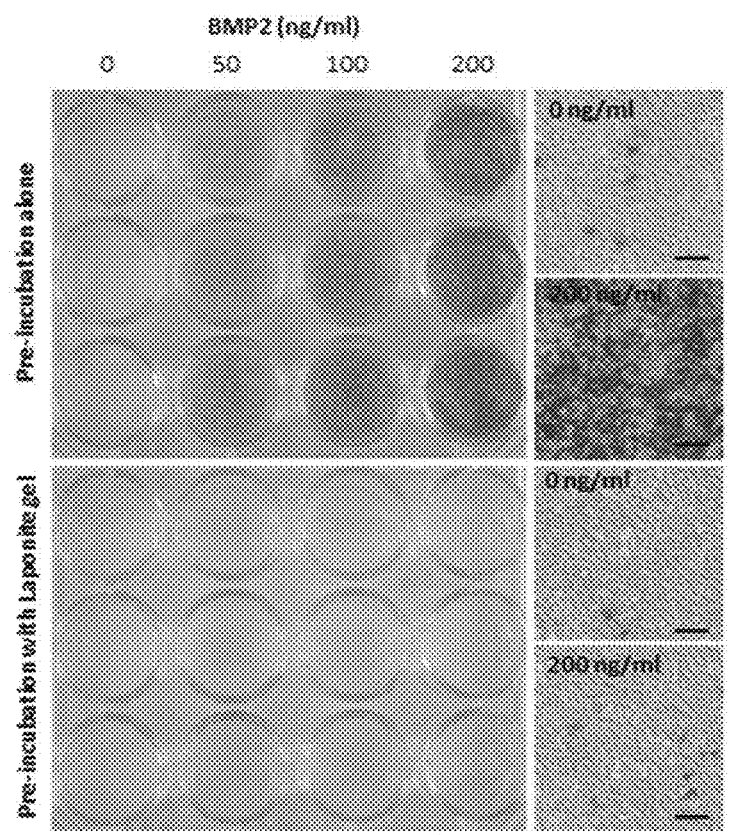
Figure 10B:
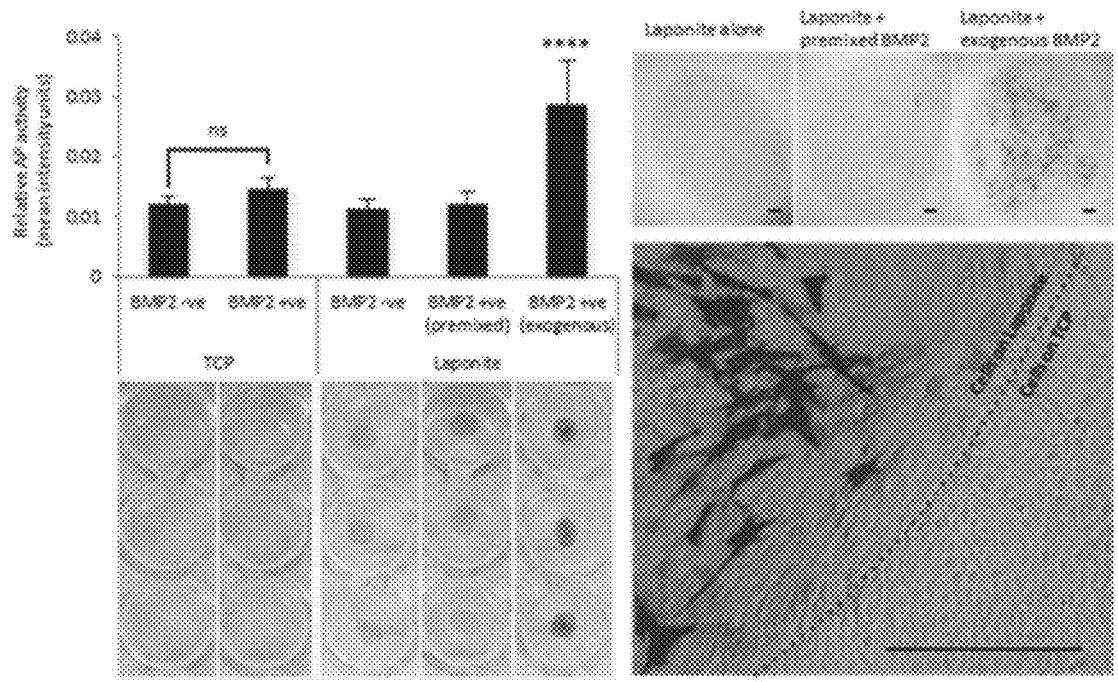

FIGS. 10A-10B show clay gels localise BMP2 for enhanced effect in vitro. FIG. 10A shows pre-incubation of BMP2 solutions in the presence of clay gel capsules eliminates the characteristic ALP dose response to BMP2 by C2C12 cells. FIG. 10B shows spotted and dried clay films enhanced ALP activity at doses below that required under standard culture conditions. Enhanced ALP activity was observed when BMP2 was added exogenously to the media but not when premixed with clay. Inset shows enhanced AP activity to be localised to cells growing directly upon clay films. Scale Bar=200 um.

Figure 11A:
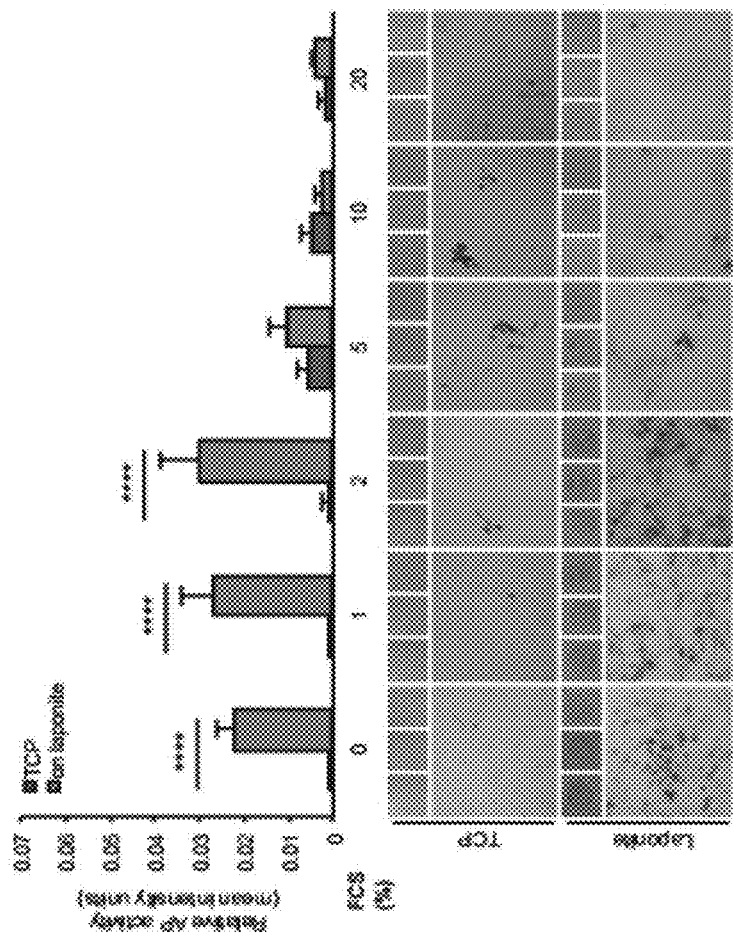
Figure 11B:
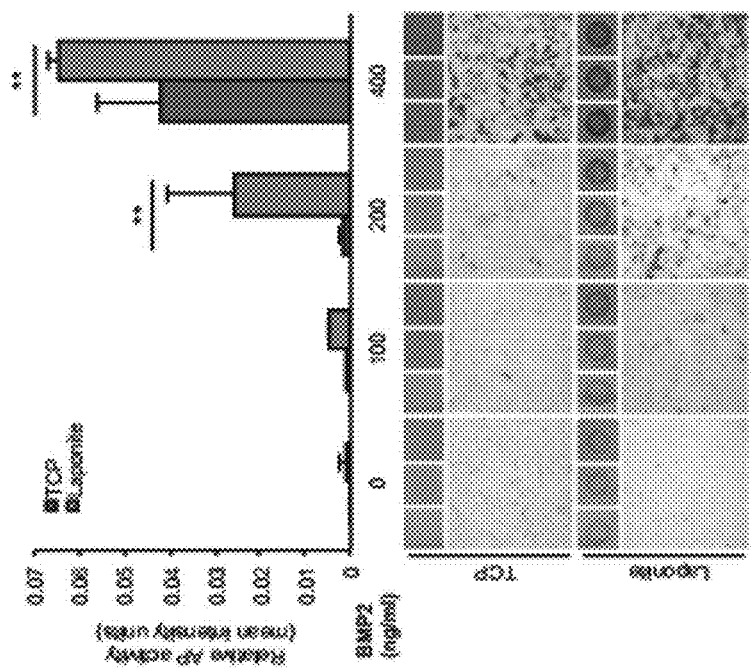
Figures 11C, 11D:
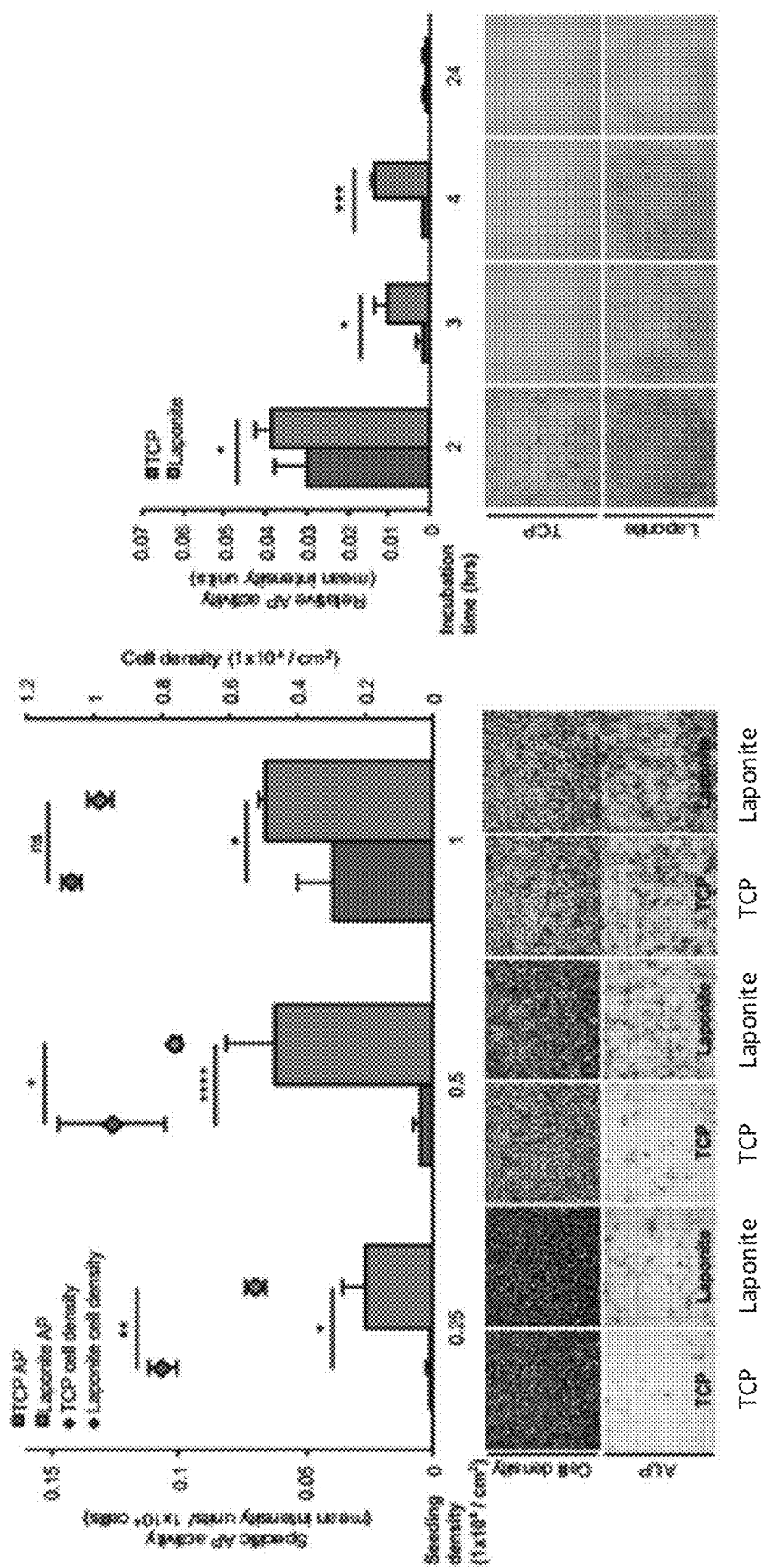
Figure 12D:
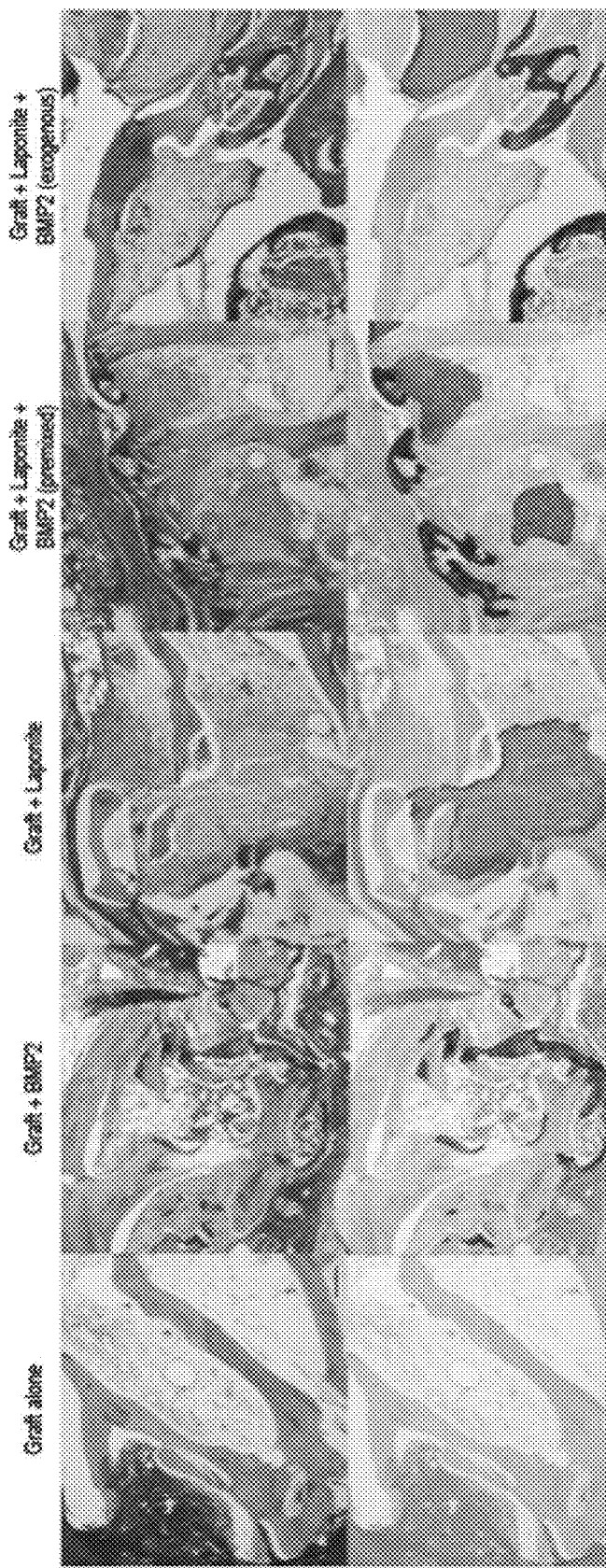

FIGS. 11A-11D show the effect of BMP2 and FCS concentration, cell density and BMP2 preincubation time on ALP activity upon clay films. Clay gel enhancement of ALP is BMP2 dose dependent (FIG. 11A) attenuated by excess fetal calf serum (FIG. 11B) independent of cell density (FIG. 11C) and prolonged over time in association with clay gels. Presence of Laponite film increased ALP activity following incubation of BMP for 2-4 hours prior to cell seeding (FIG. 11D).

FIGS. 12A-12D show BMP2 loaded clay gels functionalise non-viable bone graft to enhance osteogenesis in vitro and in vivo. Pre-coating non viable trabecular bone graft with clay gel enhances the ALP activity in seeded cells in response to BMP2 (bottom) compared to uncoated bone graft (top). Laponite gels localise labelled protein (BSA) within the trabecular structure of bone graft both when premixed with laponite and when added exogenously in PBS. In vivo, enhanced bone formation was observed with bone graft perfused with Laponite with BMP-2 compared to BMP2 alone and bone alone. This was the case whether BMP-2 solution was premixed with Laponite or applied exogenously to Laponite perfused graft at point of implantation.

Figure 13:
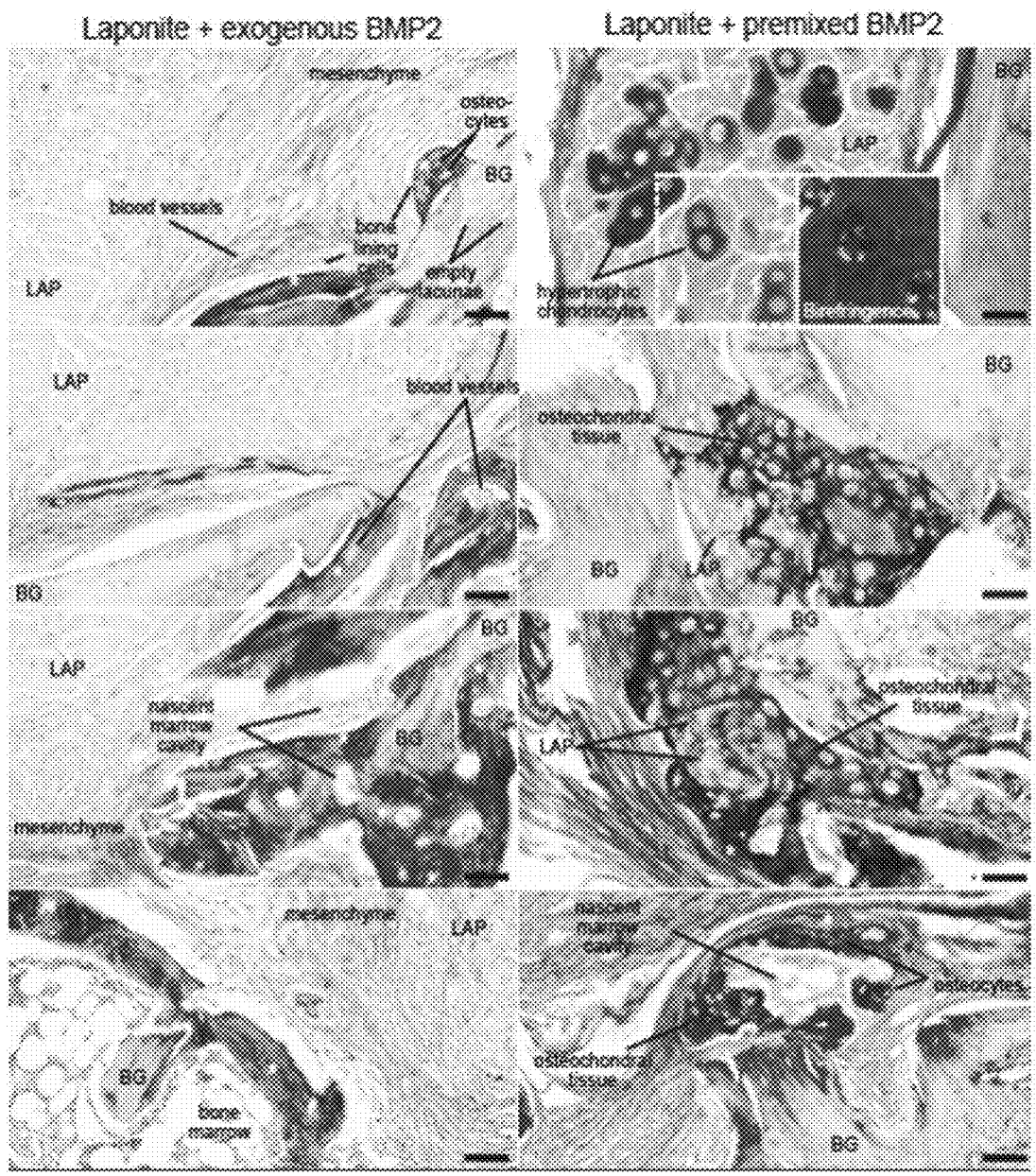

FIG. 13 shows alternate modes of BMP-2 loading in clay gels induce alternate modes of ectopic ossification. Direct, appositional bone formation was observed upon bone graft surfaces (and enhanced by Laponite gel) in response to exogenously applied BMP-2. This was in contrast to endochondral ossification observed, localised within Laponite gels, in response to premixed BMP-2. LAP=Laponite gel, BG=Bone Graft. Scale bar=50 um.

Figure 14A:
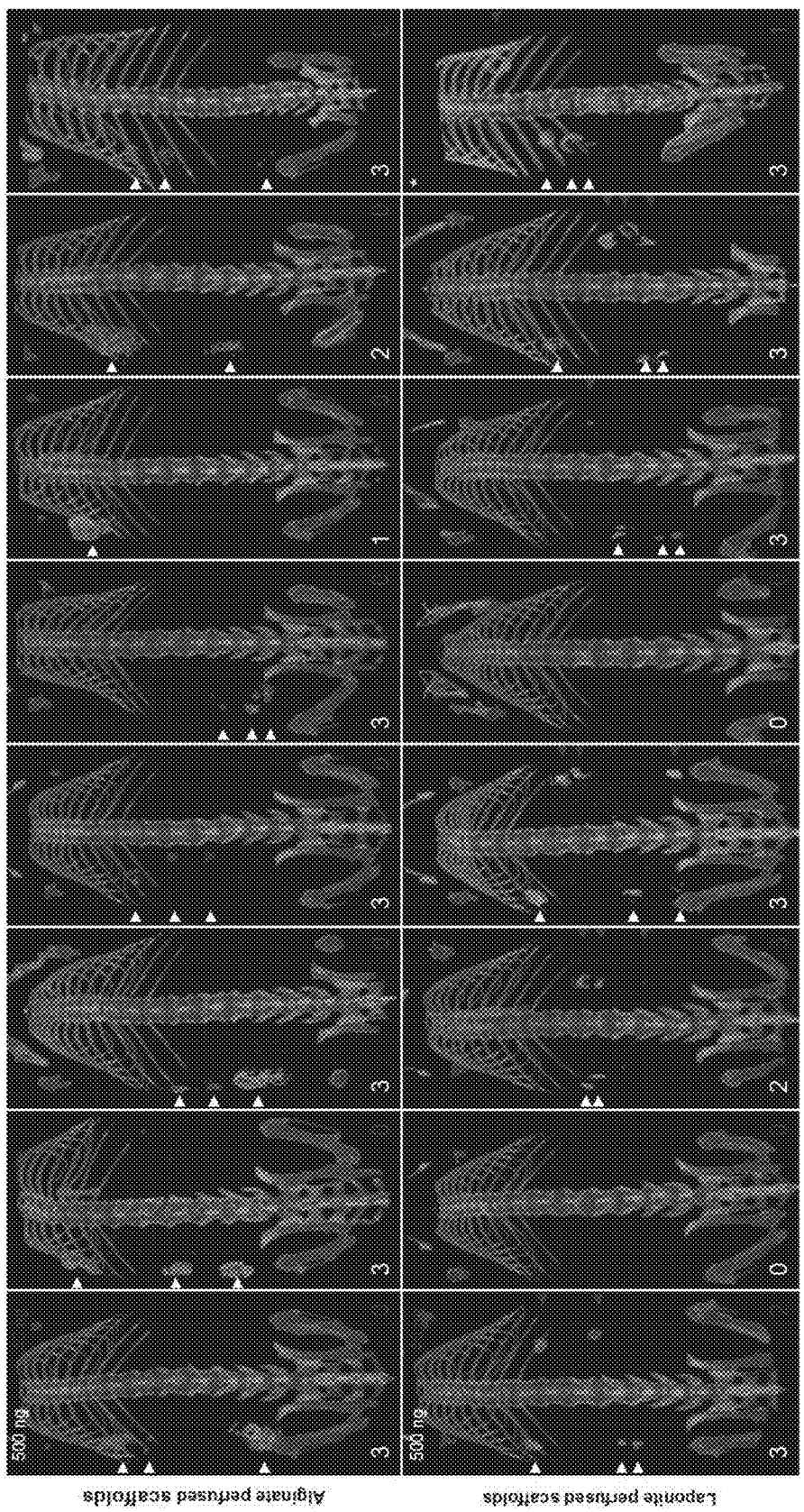

FIGS. 14A-14D show that only Laponite, not alginate, sustains ectopic bone formation at low doses of BMP2. 500 ng and 40 ng doses of BMP2 were premixed with Laponite or Alginate gels and perfused through a collagen sponge. Both contingency analysis of total numbers (FIG. 14B) and median scaffolds implanted per mouse (FIG. 14C) show increased chance of bone formation in laponite vs. alginate at low but not high dose of BMP2. Significantly greater bone volume per ng BMP was achieved with 'super low' doses of BMP2 in Laponite, compared to alginate and Laponite gels with low dose' BMP (FIG. 14D). Ectopic bone formation was observed with Alginate and Laponite containing 7 ng/ul BMP, however at least the lower dose of BMP, bone formation was only seen with Laponite (FIGS. 14A-14C).

METHODS AND MATERIALS

Determination of Interactions Responsible for Cross-Linking Between HA-BP Macromolecules and Laponite Nanoparticles (NPs). HA-BP•Laponite Hydrogel Rheology and Interaction Study Bisphosphonate (BP) groups were linked to hyaluronic acid of molecular weight 150 kDa via either stable thioether linkages (thereafter named as HA-(BP)$_3$) or labile disulfide linkages (thereafter named as HA-SS-BP). Structures of the derivatives are given in FIGS. 1A-1D. Gels were provided according to the following compositions ($DS_{BP}$ designates degree of substitution with bisphosphonate groups):

Example 1

6 mg of HA-SS-BP ($DS_{BP}$=25%) was dissolved in 150 μL H$_2$O, while 3 mg Laponite was separately dissolved in 150 μL H$_2$O. The obtained aqueous solutions were mixed affording a composition of 2% HA and 1% Laponite. This composition was designated as L001.

Example 2

6 mg of HA-SS-BP (DS=25%) was dissolved in 150 μL H$_2$O, while 6 mg Laponite was separately dissolved in 150 μL H$_2$O. The obtained aqueous solutions were mixed affording a composition of 2% HA and 2% Laponite. This composition was designated as L002.

Example 3

Thiol-terminated bisphosphonate derivative (BP-SH in FIG. 2) was prepared also to assess interactions of low molecular weight bisphosphonates with clay nanoparticles. It was expected that interaction of clay nanoparticles with BP-SH should functionalize the nanoparticles with thiol groups. Hyaluronan modified with dithiopyridyl groups (HA-SSPy in FIG. 2) was prepared to figure out about thiol functionalization of the nanoparticles through a simple gel test. For that, 6 mg Laponite was dissolved in 150 μL H$_2$O and 1.7 mg of HS-BP was added to the obtained nanoparticles solution. The resulting Laponite •BP-SH mixture was stirred for 30 min. Separately, a solution of HA-SSPy (6 mg, $DS_{SSPy}$=25%) in 150 μL H$_2$O was prepared. The obtained aqueous solution of HA-SSPy was mixed with Laponite•BP-SH mixture affording a composition of 2% HA and 2% Laponite. This composition was designated as L003 (FIG. 2).

Example 4

Another derivative of HA that is reactive to thiols, HA-allyl, was also prepared (FIG. 3). Analogously to example 3, Laponite•BP-SH mixture was prepared by dissolving 6 mg Laponite in 150 μL H$_2$O and adding 1.7 mg of HS-BP to the solution, followed by stirring for 30 min. After that, a solution of HA-allyl (6 mg, $DS_{allyl}$=15%) in 150 μL H$_2$O was added to the solution of Laponite•BP-SH. This composition was designated as L004 (FIG. 3).

Example 5

0.4% solution of free radical initiator Irgacure 29596 was prepared first. Laponite was dissolved in 150 μL initiator solution and 1.7 mg of HS-BP was added to the obtained nanoparticles solution. The resulting Laponite •BP-SH mixture was stirred for 30 min. Separately, a solution of HA-allyl (6 mg, $DS_{allyl}$=15%) in 150 μL initiator solution was prepared. The obtained aqueous solution of HA-allyl was mixed with Laponite•BP-SH mixture and then exposed to UV light for 10 minutes (36W UV timer lamp, CNC international BV, Netherlands). This composition was designated as L005 (FIG. 3).

Example 6

6 mg of HA-(BP)$_3$ ($DS_{BP}$=7×3=21%) was dissolved in 150 μL H$_2$O, while 6 mg Laponite was separately dissolved in 150 μL H$_2$O. The obtained aqueous solutions were mixed affording a composition of 2% HA and 2% Laponite. This composition was designated as L006.

Example 7

40 mg Laponite was dissolved in 500 μL H$_2$O and the nanoparticles solution was pre-incubated with 63.7 mg Na$_4$P$_2$O$_7$·10H$_2$O in 500 μL H$_2$O for 1 hour. 150 μL of the above solution containing 6 mg Laponite and 9.555 mg Na$_4$P$_2$O$_7$·10H$_2$O was then mixed with the solution of HA-(BP)$_3$ (6 mg, $DS_{BP}$=7×3=21%) in 150 μL H$_2$O affording a composition of 2% HA and 2% Laponite. This composition was designated as L007. Assuming molecular weight of Laponite (Na[(Si$_8$Mg$_{5.5}$Li$_{0.3}$)O$_{20}$(OH)$_4$]) to be 770.75 mg/mmol, 6 mg (6 mg/770.75 mg/mmol=7.79 μmol) of Laponite should contain 7.79 μmol×5.5=42.845 μmol of Mg$^{2+}$ ions. This amount of Laponite was pre-treated with 9.555 mg (9.555 mg/446.06 mg/mmol=0.0214 mmol=21.4 μmol) of Na$_4$P$_2$O$_7$·10H$_2$O. Therefore, the ratio of Mg$^{2+}$ in Laponite to P$_2$O$_7^{4-}$ was 2:1, i.e. half of magnesium ions could be screened by pyrophosphate ions and thus unavailable for interaction with BP groups.

Example 8

Solution of HA-(BP)$_3$ (6 mg, DS=7×3=21%) in 100 μL H$_2$O was pre-incubated with 18.6 mg MgCl$_2$ in 50 μL H$_2$O for 1 hour. During incubation viscosity of the solution was increased indicating coordination of BP groups on HA to soluble Mg$^{2+}$ ions. Solution of 6 mg Laponite in 150 μL H$_2$O was then mixed with the above solution affording a composition of 2% HA and 2% Laponite. This composition was designated as L008. 6 mg of HA-(BP)$_3$ used in the experiment contained 6 mg/400 mg/mmol×0.21=0.00315 mmol of BP groups. Therefore, the ratio of free Mg$^{2+}$/BP was 18.6 mg/95.22 mg/mmol/0.00315 mmol=62:1. On the other hand, the ratio of free Mg$^{2+}$ to the amount of Mg$^{2+}$ in Laponite nanoparticles was 4.55:1.

The formed gels were set for 4 to 6 days and examined by rheology measurements (before swelling). After rheology measurements, the gels were incubated in PBS for another 24 hours. The equilibrated gels were again examined by rheology measurements (after swelling). The rheology measurements are provided in Table 1 below.

TABLE 1

| Hydrogel | Before swelling | | | After swelling | | |
| --- | --- | --- | --- | --- | --- | --- |
| | Mass, mg | G', Pa | G", Pa | Mass, mg | G', Pa | G", Pa |
| L001 | 230.0 | 526 | 81 | 263.4 | 395.6 | 36.7 |
| L002 | 227.4 | 1064 | 180 | 203.8 | 585 | 60.0 |
| L003 | 208.2 | 1489 | 34 | 252.4 | 1942 | 88.0 |

TABLE 1-continued

| Hydrogel | Before swelling | | | After swelling | | |
|---|---|---|---|---|---|---|
| | Mass, mg | G', Pa | G", Pa | Mass, mg | G', Pa | G", Pa |
| L005* | 187.0 | 1247 | 86 | 158.8 | 912 | 43.0 |
| L006 | 237.0 | 5660 | 241 | 269.7 | 5669 | 206 |
| L007 | 232.7 | 2277 | 29 | 273.0 | 3638 | 83.5 |
| L008 | 229.0 | 6400 | 618 | 213.7 | 4235 | 396 |

*Part of the mixture was not cross-linked most probably due to poor light penetration (UV illumination was performed in plastic syringe with only one side opened for direct light exposure). Therefore, the mass of the gel (187 mg) was less than the average mass of other gels (227 mg).

Conclusions for Rheology Study

1) Use of Laponite with higher concentration (2% vs. 1%) affords stronger gels as exemplified by gels L002 (G'=1064 Pa) and L001 (G'=526 Pa).

2) Thiol-ene photo-chemical addition of BP-acrylamide to HA-thiol provides an attachment of approximately three BP groups to one thiol group of HA. This results in a brush-like arrangement of BP groups along the HA backbone, as in HA-(BP)$_3$ derivative. Oppositely, disulfide attachment of BP-thiol reagent to HA-SSPy derivative results in tethering of only one BP group to a side chain of the HA backbone, as in HA-SS-BP derivative (FIG. 1C). Moreover, BP groups are attached though more labile disulfide linkages in HA-SS-BP derivative. Eventually, the use of HA-(BP)$_3$ (DS$_{BP}$=21%) derivative afforded much stronger gel L006 (G'=5660 Pa) than the use of HA-SS-BP (DS$_{BP}$=25%) which yielded gel L002 (G'=1064 Pa).

3) When Laponite nanoparticles were pre-incubated with pyrophosphate ions prior to mixing with HA-(BP)$_3$, it weakened twice interactions between polymeric HA component and the inorganic nanoparticles (5660 Pa and 2277 Pa for gels L006 and L007 respectively before swelling). After swelling in PBS, the difference in elastic modulus between the gels becomes less (5669 Pa and 3638 Pa for gels L006 and L007 respectively). These observation confirmed participation of Laponite Mg$^{2+}$ ions in interaction with HA polymer. Since pyrophosphate is known to interact with Laponite Mg$^{2+}$ ions as well as bisphosphonates are analogs of pyrophosphates, it indicates that pyrophosphates most probably displace BPs of HA-(BP)$_3$ from interactions with Mg$^{2+}$ ions located on edges of Laponite NPs. Swelling of gel L007 in PBS should cause diffusion of pyrophosphates from the gel, their elimination from competing interactions with BPs, and subsequently to strengthening of the gel.

4) Oppositely, pre-incubation of HA-(BP)$_3$ with MgCl$_2$ followed by mixing with Laponite NPs only made the resulting gel L008 stronger (G'=6400 Pa) as compared with gel L006 (G'=5660 Pa). It seems that Mg$^{2+}$ ions in solution participates in additional bridging interactions between Laponite NPs and HA-(BP)$_3$ polymer rather than displacing BP groups from interactions with Laponite Mg$^{2+}$ ions. Further swelling of gel L008 in PBS eliminated free Mg$^{2+}$ ions from the gel and softened the gel (G'=4235 Pa), while almost no change in elastic modulus occurred upon swelling of gel L006 (G'=5669 Pa) which was prepared in pure water.

5) BP groups on HA polymer are indeed responsible for direct interactions with Laponite NPs and formation of physical gels. This was demonstrated by studying gels L002, L003, and L005. Gel L002 was formed as a result of physical interactions between HA-SS-BP polymer and Laponite NPs. This physical gel can essentially be depicted as HA-SS-BP•Laponite. We hypothesized that similar gel structure can be obtained using a chemical thiol-disulfide exchange reaction between polymeric HA-SSPy derivative (FIG. 2) and Laponite•BP-SH, assuming that thiol-functionalized Laponite NPs are indeed generated upon interaction between Laponite NPs and thiolated low molecular weight bisphosphonate HS-BP (FIG. 2). Chemical structure of HS-BP is rather simple permitting limited number of options for interactions with Laponite NPs and only interaction through BP side leaves thiol groups free for chemical cross-linking. Moreover, thiol-decorated Laponite NPs should participate in all reactions peculiar to thiols. Therefore, gel L005 was formed upon photo-initiated thiol-ene addition reaction of Laponite•BP-SH to allyl-derivatized HA. It is noteworthy that no gel was formed without UV light (composition L004). In general, treatment of Laponite with low molecular weight BPs screens positively charged edges of Laponite NPs excluding them from interactions described by a "playing cards" model of Laponite gel.

Hydrogel Degradation Study

Gels L001, L002, L003, L005, and L006 were divided into two parts:

L001-1 (104.2 mg) and L001-2 (128.3 mg)

L002-1 (96.4 mg) and L002-2 (97.4 mg)

L003-1 (102.2 mg) and L003-2 (93.1 mg)

L005-1 (58.9 mg) and L005-2 (66.9 mg)

L006-1 (120.9 mg) and L006-2 (128.0 mg)

First parts of the gels L001, L002, L003, L005, and L006 as well as gels L007 and L008 were washed by repeated swelling in pure water (3×20 min and 1×16 hours). These samples were analyzed by scanning electron microscopy and images are shown in FIGS. 4A-4D.

Second parts of the gels L001, L002, L003, L005, and L006 were treated with 5 mL of 40 mM dithiothreitol (DTT) for 16 hours. Gels L001-2, L002-2, and L003-2 were dissolved, while gels L005-2 and L006-2 were intact. These results again confirmed that physical gels were formed due to interactions of BP groups on HA polymers with Laponite NPs. Thus, in HA-(BP)$_3$—Laponite gel (L006), the linkage between HA backbone and BP groups cannot be cleaved with DTT. It is also true for the gel formed by photo-initiated thiol-ene cross-linking of Laponite•BP-SH nanoparticles with HA-allyl derivative (i.e. L005). The thioester bond that is formed between Laponite NPs and HA macromolecules in this case is insensitive to DTT. However, HA-SS-BP•Laponite gels (L001, L002, and L003) have labile disulfide bond between the HA backbone and BP groups of HA polymers. Treatment with DTT can hence disconnect Laponite NPs from HA polymers and thus disassemble the hydrogel in the case of coordination bonding of Laponite NPs to BP groups on HA but not, for example, to HA carboxylate groups (FIGS. 5A-5B).

The dissolved gels L001-2, L002-2, and L003-2 were filtered through a glass wool to remove some remaining visible parts of hydrogels and then examined by DLS (dynamic light scattering).

Digest from L001-2 (FIG. 6A)

Z-Average (d.nm): 158.4 nm

PDI: 0.29

Intercept: 0.949

Result quality: Good

Digest from L002-2 (FIG. 6B)

Z-Average (d.nm): 211.7 nm

PDI: 0.447

Intercept: 0.944

Result quality: Good

Digest from L003-2 (FIG. 6C)
  Z-Average (d.nm): 204.5 nm
  PDI: 0.352
  Intercept: 0.943
  Result quality: Good
  For comparison, 150 µL of 4% Laponite was diluted with 5 mL water and then examined by DLS:
Laponite NPs in water (FIG. 6D)
  Z-Average (d.nm): 60.18 nm
  PDI: 0.364
  Intercept: 0.950
  Result quality: Good
  Finally, 6 mg Laponite in 150 µL H$_2$O was treated with 1.7 mg of HS-BP for 30 min to give Laponite•BP-SH (conditions of preparation of gel L003, FIG. 2). Laponite•BP-SH was then diluted with 5 mL water and then examined by DLS:
Laponite•BP-SH in water (FIG. 6E)
  Z-Average (d.nm): 53.65 nm
  PDI: 0.218
  Intercept: 0.41
  Result quality: Good
Conclusions for DLS Study
  1) Design of disulfide linkage between backbone of HA polymer and BP group allowed mild disassembly of the corresponding hydrogels. It was expected to obtain the size of NPs after gel disassembly similar to the size of original Laponite NPs. However, the size of hydrogel-derived NPs was in the range 160-210 nm versus 50-60 nm for original Laponite NPs. Exact calculations revealed only one BP group per 2.5 nanoparticles of Laponite (3.15 µmol of BP groups in 6 mg of HA-(BP)$_3$ and 7.79 µmol of nanoparticles in 6 mg of Laponite, i.e. 7.79/3.15≈2.5). This means that not a single Laponite nanoparticle but rather a cluster of Laponite NPs, associated through electrostatic interactions, can function as a difunctional cross-linker for HA macromolecules. In other words, both inherent electrostatic association of Laponite NPs as well as coordination of bisphosphonated HA polymer to the Laponite associates through BP•Mg$^{2+}$ coordination may take place during mixing of the organic and inorganic components leading to the formation of physical gel.
  2) Laponite NPs at higher concentrations associate into larger clusters as can be seen from disassembly of gels L001 versus L002.
  3) It is noteworthy that physical [HA-SS-BP+Laponite NPs L002] and chemical [HA-SSPy+Laponite•BP-SH→L003] pathways give the hydrogels of the same HA-SS-BP•Laponite structure. Disassembly of gels L002 and L003 should give the same Laponite•BP-SH NPs which was indeed confirmed by DLS study (211.7 nm and 204.5 nm for Laponite•BP-SH NPs derived from gels L002 and L003 respectively).
Cytochrome c (Cyt c) loading and release studies
  In this study, the new invented physical hydrogel was compared with its chemical HA analogues either containing or not containing BP groups. For this purpose, several HA derivatives were prepared containing different appended functional groups: aldehyde-modified HA (HA-al), hydrazide-modified HA (HA-hy), and hydrazide and bisphosphonate dually modified HA (HA-BP-hy). The synthesis and structure of all these derivative has been documented by us previously (Xia Yang. et al. (2012) *Chemistry of Materials* 24, no. 9: 1690-1697). Hydrazone cross-linked hydrogels can be obtained upon mixing of aqueous solutions of HA-al with either HA-hy or HA-BP-hy.

40 mg of solid Laponite NPs were added under vigorous stirring to 1 mL water and stirring was continued until complete dissolution of the NPs. This afforded 4% Laponite solution.
Four types of hydrogels were prepared:
  1) HA-BP•Laponite physical gel by mixing of 6 mg HA-BP in 150 µL H$_2$O and 6 mg Laponite in 150 µL H$_2$O.
  2) HA-BP chemical gel by mixing of 3 mg HA-BP-hy in 150 µL H$_2$O and 3 mg HA-al in 150 µL H$_2$O.
  3) HA chemical gel by mixing of 3 mg HA-hy in 150 µL H$_2$O and 3 mg HA-al in 150 µL H$_2$O.
  4) Laponite physical gel by dissolving 34 mg Laponite in 850 µL H$_2$O
  Gels 1)-3) were formed in three syringe molds and allowed to set for almost 24 hours. Degree of hydrazide modification in HA-BP-hy and HA-hy was the same (10%) which ensured the same cross-linking density on two chemical gels. On the other hand, Amount of HA was also kept the same in all three hydrogel samples (2%). Degree of bisphosphonate modification in HA-BP and HA-BP-hy was the same (8%). Gel 4) was formed in a vial upon standing the 4% Laponite solution overnight.
Mechanical properties of hydrogels after setting.
  Hydrogel 1), m(hydrogel)=266 mg, G'=1150 Pa
  Hydrogel 2), m(hydrogel)=260 mg, G'=401 Pa
  Hydrogel 3), m(hydrogel)=230 mg, G'=1260 Pa
  G' values are shown for frequency 0.5 Hz. Normal force on hydrogels was between 0.015 and 0.02. Chemical HA hydrogel was stronger than chemical HA-BP hydrogel which can be attributed to the repulsive forces between BP groups for HA-BP hydrogel.
Loading Cyt c to Hydrogels 1)-3).
  10 mg of Cyt c was dissolved in 10 mL PBS and 3 mL of the prepared solution was added to each hydrogel sample. The hydrogels were equilibrated in the Cyt c solution for 5 days.
Loading Cyt c to Hydrogel 4).
  3 mg Cyt c/3 mL PBS was added to 277 mg of hydrogel 4). The hydrogel was equilibrated in the CytC solution for 3 days.
  Images of hydrogels as well as images of the corresponding Cyt c feeding solutions after loading are shown in FIG. 8A.
Release of Cyt c from Hydrogels.
  Hydrogels 1)-4) were placed in 3 mL of PBS after completion of CytC loading by diffusion. At certain intervals of time, PBS medium was withdrawn from the hydrogels and replaced with the fresh one. The collected samples of the release media were later evaluated by UV-Vis spectrophotometry (FIG. 8B).
Clay Nanoparticle Gels Localise and Enhance the Efficacy of BMP Induced Bone Formation
  Every year over 2 million people suffer a fracture in the UK alone, while the majority heal uneventfully, in fractures of the lower limb, patients often require 2-4 months off work and in high energy injuries of the tibia up to 40% do not heal. Spinal fusion or arthrodesis is a key treatment in the management of a range of conditions including: scoliosis, degenerative disc disease, spinal stenosis, and trauma. In the last decade rates of spinal fusion in the USA have increased by 137%. Autologous bone grafting (ABG) is considered the gold standard therapy in treatment of fracture non-union, and in mediating spinal fusion. ABG is associated with patient morbidity and volume of graft available is strictly limited. Allograft and synthetic bone products have been developed to replace ABG, however they lack osteogenicity and are less effective in mediating fracture union and arthrodesis than ABG.

Bone Morphogenetic Protein is a growth factor which has been used in clinical practice to replace ABG and stimulate fracture healing and spinal fusion. In clinical practice solubilized BMP is applied as a solution onto a collagen sponge and placed at the fracture or fusion site, around 50% of the BMP is released within 3-6 days, as a consequence relatively large doses are required. Studies have demonstrated significant adverse effects with BMP use such as: Heterotopic ossification, osteolysis, and swelling which were associated with the dose of BMP used. Development of a highly efficient BMP delivery vehicle offers the potential to reduce the effective dose of BMP, facilitating fracture healing and arthrodesis without precipitation of serious adverse effects.

Smectities, are a group of synthetic clays, the unit structure of which consists of two tetrahedral silica sheets sandwiching an octahedral sheet composed of Aluminium or Magnesium. Upon hydration Smectites delaminate to form thixotropic gels, with the charged Smectite sheets giving rise to multiple sites for protein binding. Laponite, has been used in the pharmaceutical industry, and is considered non-toxic.

This study validates the ability of Laponite to localize the activity of exogenously applied BMP in vitro, and enhance the activity of BMP mediated bone formation in vivo.

Clay Gels Localise the Activity of Exogenously Applied BMP In Vitro

The response of C2C12 cells (a myoblastic cell line) to BMP-2 premixed with media or Laponite prior to cell seeding was previously investigated. C2C12 cells cultured on BMP premixed in media demonstrated a characteristic increase in Alkaline Phosphatase (ALP) Activity[13], whilst BMP-2 premixed with Laponite did not (FIG. 10A). In contrast, exogenous application of BMP in the media resulted in localisation of ALP activity to the clay (FIG. 1B). Laponite is known to adsorb proteins. It appears that BMP-2 premixed with Laponite is bound within the clay and unavailable to cells, whilst with exogenous application BMP is localised to the surface of the clay and thus able to stimulate C2C12 cells as observed in FIG. 10B. No effect of Laponite on viability of C2C12 cells or Human Bone Marrow Stromal Cells (HBMC) was observed. In contrast to previous work[14,15] no intrinsic osteogenic effect of Laponite on HBMC was identified. This discrepancy is likely to be due to variation in Laponite preparations employed, Wang[14] utilised sintered Laponite whilst Gaharwar[15] applied Laponite to a solution in contrast to dry Laponite films in the present study.

Clay Gels Enhance and Prolong Activity of BMP In Vitro

Presence of clay was observed to enhance the cellular response to increasing concentrations of exogenous BMP (FIG. 11A). A differential cellular response to Fetal Bovine Serum (FBS) was observed on Laponite, with ALP activity peaking at 2% and 5% FBS for Laponite and tissue culture plastic (TCP) respectively. Laponite has been shown to exhibit preferential protein binding[16], it is postulated that the different effect of FBS in presence of Laponite may result from displacement of Laponite bound BMP.

In order to define if increased ALP activity on Laponite films resulted from an effect of cell density or activity per cell the response of ALP activity to cell seeding density on Laponite and TCP was characterised. ALP activity was proportional to cell seeding density on both Laponite and TCP, however, through the range tested cell density and ALP activity per cell was greater on Laponite (FIG. 11C). This demonstrated ALP activity per cell was increased, with reduced cell density on Laponite likely to be secondary to BMP mediated stimulation of differentiation at the expense of proliferation. Presence of Laponite film increased ALP activity following incubation of BMP for 2-4 hours prior to cell seeding (FIG. 11D). The demonstrated increased ALP activity in the presence of Laponite could be either secondary to modulated BMP activity, or an effect of Laponite on BMP localisation, in the context of previous work[12] the latter is more likely.

Clay Bound BMP Enhances Allograft Bone Formation

Laponite gel was observed to maintain BMP and labelled Bovine Serum Albumin (BSA) to allograft despite undergoing a saline wash (FIGS. 12A and 12B). In the absence of Laponite BMP and BSA were readily displaced from allograft during washing. The ability of Laponite gel to enhance bone formation on acellular allograft mediated by 1 ug BMP per implant in a murine mode was subsequently investigated. Allograft cylinders were implanted subcutaneously in nude mice and loaded with: (i) BMP, (ii) Laponite gel, (iii) Laponite with premixed BMP, (iv) Laponite and exogenous BMP, or (v) left blank. MicroCT performed prior to implantation and at 28 days demonstrated that increase in bone volume was significantly greater with BMP applied in the presence of Laponite, compared to BMP with allograft (FIG. 12C).

Application of BMP to allograft resulted in reduction of increase in bone volume compared to allograft alone. In addition to stimulating osteogenesis, BMP is also known to stimulate osteolysis[17] and it is postulated the relative effect upon these opposite processes is dependent on magnitude and rate of BMP delivery. Histological analysis failed to show any new bone on allograft in the absence of BMP. Whilst some new bone was observed with allograft and BMP, more areas of new bone formation were evident in the presence of BMP and Laponite (FIG. 12A-12D). Modulation of BMP release by the Laponite may result in a predominately osteogenic response as opposed to osteolytic when BMP is delivered in isolation. In concordance with the in vitro work, Laponite alone, was not seen to have an osteogenic effect. There was no significant difference of increase in allograft bone volume with Laponite and premixed BMP-2 or Laponite and exogenous application of BMP-2 on micro CT. However, on histological analysis exogenous BMP appeared to promote appositional bone formation, whereas endochondral bone formation predominated when BMP-2 was premixed with the Laponite gel prior to application (FIG. 13).

The in vitro results suggest premixing results in BMP localisation within the gel, if this replicated in vivo only osteoprogenitor cells present within the gel may be activated by the BMP, in contrast to exogenous BMP which is available to stimulate cells on the surface of the gel. The difference in biomechanical and biological environments within the gel and on the gel surface may explain the stimulation of endochrondral and appositional osteogenesis observed in Laponite with premixed and exogenously applied BMP, respectively.

Clay Gels Reduce the Dose of BMP Required for Ectopic Bone Formation

It was next investigated if Laponite gel was able to reduce the dose of BMP required to stimulate bone formation. BMP was mixed in Laponite and Alginate to produce gels containing 7 ng/ul and 0.57 ng/ul BMP. Gels were absorbed by collagen sponge cylinders and implanted subcutaneously in MF-1 mice. Bone volume was assessed fortnightly, and at 8 weeks histological analysis was performed. It was chosen to deviate from clinical method of BMP delivery by using Alginate gel and collagen in lieu of collagen alone as this enabled comparison of Laponite with another hydrogel, rather than water. Alginate has a proven track record in growth factor delivery[18] and has been shown to mediate BMP delivery more efficiently than collagen alone[19]. Ectopic bone formation was observed with Alginate and Laponite containing 7 ng/ul BMP, however at the lower dose of BMP, bone formation was only seen with Laponite (FIGS. 14A-14C).

Bone volume formed per ug BMP was significantly greater with Laponite and low dose BMP compared to alginate with high or low dose BMP (FIG. 14D). Volume of gel loaded onto individual collagen cylinders was recorded, and bone volume produced per unit BMP expressed graphically (FIG. 14D). Bone volume was directly proportional to BMP with Laponite and low dose BMP, while no correlation was seen with gels and high dose BMP. These results are suggestive that the in vivo response to BMP was saturated with gels containing high dose BMP, this observation is supported in the literature; Boerckel[19] reported a dose dependent increase in bone volume as BMP was increased from 6.37 to 31.83 ug/cm$^3$ at a rat femoral defect, and Peleaz[20] found that stimulation of bone formation in a rat calvarial defect was saturated around 25-50 ug/cm$^3$. Inter-study comparison of BMP dosing is inherently challenging due to variation in BMP preparation and the plethora of species and in vivo models employed[18]. To facilitate comparison of BMP doses used in this study BMP doses are expressed as ug BMP per volume of defect (cm$^3$) from some key publications (table 1). This study, in which Laponite hydrogel was used as a delivery vehicle, demonstrates the lowest recorded BMP dose to stimulate ectopic bone formation, an environment which is considerably less osteogenic than orthotopic, or spinal fusion models such as employed by Lee[21], in which the defect is adjacent to bleeding bone.

The ability of Laponite to localise and enhance BMP activity in vitro was shown, while the in vivo study demonstrated that BMP delivered by Laponite stimulated ectopic bone formation at BMP doses approximately 3000 fold smaller than those employed in clinical practice. There is exciting potential of Laponite to safely harness the powerful osteogenic effect of BMP thus facilitating treatment of thousands of patients suffering from non-union of fractures or spinal arthrodesis.

Methods

Laponite Preparation

Laponite gel was prepared as described previously[12]. Briefly, Laponite XLG powder was dissolved in distilled water to required concentration % weight Laponite per unit volume. Laponite gel was subsequently sterilised by autoclave and evaporated water replaced. To produce dry Laponite films for cell culture 5 ul of 1% Laponite was placed on TCP and permitted to dry for 2 hours at room temperature prior to cell seeding.

Cell Culture and Analysis of ALP Activity

Unless stated otherwise C2C12 cells were seeded at 1×10$^5$/cm$^2$ and cultured with D-MEM containing 1% Penicillin/Streptomycin, 10% FBS, and when present BMP, at 200 ng/ml. Following cell culture for 72 hours, cells were fixed in ethanol and alkaline phosphatase staining performed according to a standard protocol. Representative images were taken using Axiovert 200 microscope and Axiovision software V4.0. Cell Profiler software was used to calculate cell density and ALP staining intensity relative to Laponite or TCP according to surface used for cell culture.

Allograft Preparation

Donated human femoral heads were received from Southampton General Hospital with ethical approval. Cylinders of trabecular bone 4 mm in diameter were removed using a trephine. Samples were cut to remove any subchondral bone to form cylinders 4 mm in length. Sections of trabecular bone approximately 10×10×2 mm were also cut with a bone saw from a second femoral head. Cylinders and bone

TABLE 1

| Author | BMP carrier | Species | Model | Defect volume (uL) | Dose BMP (ug/cm$^3$) | Min. effect dose BMP (ug/cm$^3$) |
|---|---|---|---|---|---|---|
| Lee 2015[21] | Heparin based hydrogel | rat | Posterio-lateral spinal fusion | 200 | 0.5 | 0.5 |
| | Heparin based hydrogel | mouse | Ectopic (muscle) | 20 | 50 | 50 |
| Gibbs 2015 | ACS/ Laponite | mouse | Ectopic (subcutaneous) | 63 | 0.57-6.97 | 0.57 |
| Boerckel 2011[19] | PCL mesh + Alginate | rat | Femoral defect | 157 | 0.64-31.83 | 6.37 |
| | ACS | rat | Femoral defect | 157 | 0.63-15.91 | 6.37 |
| Wang 1990[22] | none | rat | Ectopic (subcutaneous) | 50 | 9.2 | 9.2 |
| Pelaez 2014[20] | ACS | rat | calvarial | 50 | 24.87-397.89 | 24.87 |
| Ben-David 2013[23] | PEG/fibrinogen hydrogel | Nude mice | Ectopic (subcutaneous) | 30 | 33.95 | 33.95 |
| Govender 2002[5] | ACS | human | Tibial fracture | | 750-1500 | 750 |

ACS, Absorbable Collagen Sponge.
PCL, Polycaprolactone.
PEG, Polyethylene Glycol sections underwent multiple washes in 5% Hydrogen Peroxide and saline to remove cells and fat.

In Vitro Allograft Studies 20 ul of 1% Laponite gel was applied to a section of acellular allograft and left to dry for 2 hours at 37° C. This allograft section, and a second allograft section which had not received Laponite, were placed in petri dishes. Media containing C2C12 cells and BMP was added and microscopy performed as described above (FIG. 12A). Allograft sections were perfused with: 19 ul Phosphate Buffered Saline (PBS)+1 ul Fluorescein labelled Bovine Serum Albumin (FITC-BSA), 20 ul 2.5% Laponite, 19 ul 2.5% Laponite+1 ul FITC-BSA, premixed with Laponite or applied exogenously following application of Laponite gel to allograft sections. Allograft sections were washed in PBS for 2 minutes, and representative images taken (FIG. 12B).

In Vivo Study of Bone Formation on Allograft

In compliance with ethical approval nude mice were anaesthetised with an intra-peritoneal injection of a midazolam/fentanyl mix. A midline dorsal incision was made, 3 allograft cylinders were implanted on each side and wounds closed with clips. Immediately prior to implantation cylinders were perfused with: 1) 20 ul PBS+1 ug BMP, 2) 20 ul 2.5% Laponite, 3) 20 ul 2.5% Laponite+1 ug BMP mixed in prior to application, 4) 20 ul 2.5% Laponite with 1 ug BMP added subsequently or 5) left blank as a control. Five mice were used in total, with n=6 for each of the 5 groups.

In Vivo Study of Bone Formation in Collagen

MF-1 mice were used, surgery and anaesthesia was performed as above. A collagen sheet 4 mm in thickness was obtained from Medtronic. From this identical cylinders of 4 mm in diameter were prepared using a skin biopsy punch in a sterile environment. BMP solution of 1 ug/ul was added to 2% Laponite and 2% Alginate to produce gels containing 7 ug/ml and 0.57 ug/ml BMP. 140 ul of the gels was transferred to individual wells of a 96 well plate. Sponge cylinders were compressed and allowed to expand while submerged in the gel filled wells. Each mouse received 3 collagen cylinders containing high dose BMP gels on the left side and 3 with low dose BMP gels on the right, one mouse received 6 blank collagen cylinders as a control. In total 17 mice were used, with n=24 for each of the 4 groups: 1) Laponite 7 ug/ml BMP 2) Laponite 0.57 uh/ml BMP 3) Alginate 7 ug/ml BMP 4) Alginate 0.57 uh/ml BMP and n=6 in group 5) collagen only. Gels were made fresh for each individual mouse during induction of anaesthesia, with BMP kept on dry ice until use. Volume of gel remaining following absorption was recorded for each individual cylinder.

Micro CT

All CT scans were performed using Brunker Skyscan 1176, images were reconstructed using NRecon, and analysed using CTAn software. Allograft cylinders were scanned prior to implantation with 50 kV voltage, 500 uA current, 0.5 mm Al filter and a pixel size of 9 um. Following implantation allograft cylinders were removed and scanned again using the same settings. The same scan settings were used during the study of bone formation within the collagen cylinders with the exception that the pixel size was increased to 18 um.

Histology

Allograft samples underwent decalcification in Histoline for 24 hours, collagen samples did not undergo decalcification. Subsequently samples were dehydrated, embedded in wax and sectioned at 9 um thickness. Alcian blue and Sirius red staining was performed according to standard protocols.

Statistical Analysis

Statistical analysis was performed using GraphPad Prism 6.0. Unpaired t-tests were used to compare ALP activity on Laponite with TCP with statistical significance determined using the Holm-Sidak method when BMP or cell seeding density were variables. For BMP incubation study 2-way ANOVA test was performed with P values adjusted to account for multiple comparisons. Fisher's exact test was used to compare number collagen scaffolds demonstrating bone formation. One-way ANOVA test was used to compare mean bone volume formed on collagen and allograft scaffolds.

REFERENCES

1 Rajaee, S. S., Bae, H. W., Kanim, L. E. & Delamarter, R. B. Spinal fusion in the United States: analysis of trends from 1998 to 2008. *Spine* 37, 67-76 (2012).

2 Blokhuis, T. J., Calori, G. M. & Schmidmaier, G. Autograft versus BMPs for the treatment of non-unions: What is the evidence? *Injury* 44, Supplement 1, S40-S42, doi:http://dx.doi.org/10.1016/S0020-1383(13)70009-3 (2013).

3 Fischer, C. R. et al. A systematic review of comparative studies on bone graft alternatives for common spine fusion procedures. *European Spine Journal*, 1-13 (2013).

4 Younger, E. M. & Chapman, M. W. Morbidity at bone graft donor sites. *J Orthop Trauma* 3, 192-195 (1989).

5 Govender, S. et al. Recombinant human bone morphogenetic protein-2 for treatment of open tibial fractures a prospective, controlled, randomized study of four hundred and fifty patients. *The Journal of Bone & Joint Surgery* 84, 2123-2134 (2002).

6 Dawson, E., Bae, H. W., Burkus, J. K., Stambough, J. L. & Glassman, S. D. Recombinant Human Bone Morphogenetic Protein-2 on an Absorbable Collagen Sponge with an Osteoconductive Bulking Agent in Posterolateral Arthrodesis with Instrumentation A Prospective Randomized Trial. *The Journal of Bone & Joint Surgery* 91, 1604-1613 (2009).

7 Uludag, H., D'Augusta, D., Palmer, R., Timony, G. & Wozney, J. Characterization of rhBMP-2 pharmacokinetics implanted with biomaterial carriers in the rat ectopic model. *Journal of Biomedical Materials Research* 46, 193-202, doi:10.1002/(sici)1097-4636(199908)46: 2<193::aid-jbm8>3.0.co;2-1 (1999).

8 Shields, L. B. et al. Adverse effects associated with high-dose recombinant human bone morphogenetic protein-2 use in anterior cervical spine fusion. *Spine* 31, 542-547 (2006).

9 Tumialán, L. M., Pan, J., Rodts Jr, G. E. & Mummaneni, P. V. The safety and efficacy of anterior cervical discectomy and fusion with polyetheretherketone spacer and recombinant human bone morphogenetic protein-2: a review of 200 patients. (2008).

10 Axelrad, T., Steen, B., Lowenberg, D., Creevy, W. & Einhorn, T. Heterotopic ossification after the use of commercially available recombinant human bone morphogenetic proteins in four patients. *Journal of Bone & Joint Surgery, British Volume* 90, 1617-1622 (2008).

11 Dawson, J. I. & Oreffo, R. O. Clay: New opportunities for tissue regeneration and biomaterial design. *Advanced Materials* 25, 4069-4086 (2013).

12 Dawson, J. I., Kanczler, J. M., Yang, X. B., Attard, G. S. & Oreffo, R. O. Clay gels for the delivery of regenerative microenvironments. *Adv Mater* 23, 3304-3308, doi: 10.1002/adma.201100968 (2011).

13 Katagiri, T. et al. Bone morphogenetic protein-2 converts the differentiation pathway of C2C12 myoblasts into the osteoblast lineage. *The Journal of Cell Biology* 127, 1755-1766, doi:10.1083/jcb.127.6.1755 (1994).

14 Wang, C. et al. Preparation of Laponite Bioceramics for Potential Bone Tissue Engineering Applications. *PloS one* 9, e99585 (2014).

15 Gaharwar, A. K. et al. Bioactive silicate nanoplatelets for osteogenic differentiation of human mesenchymal stem cells. *Adv Mater* 25, 3329-3336 (2013).

16 Pawar, N. & Bohidar, H. Surface selective binding of nanoclay particles to polyampholyte protein chains. *The Journal of chemical physics* 131, 045103-045103 (2009).

17 Helgeson, M. D. et al. Adjacent vertebral body osteolysis with bone morphogenetic protein use in transforaminal lumbar interbody fusion. *The Spine Journal* 11, 507-510, doi:http://dx.doi.org/10.1016/j.spinee.2011.01.017 (2011).

18 Gothard, D. et al. Tissue engineered bone using select growth factors: a comprehensive review of animal studies and clinical translation studies in man. *European Cells and Materials* 28, 166-208 (2014).

19 Boerckel, J. D. et al. Effects of protein dose and delivery system on BMP-mediated bone regeneration. *Biomaterials* 32, 5241-5251 (2011).

20 Pelaez, M. et al. Effect of rhBMP-2 dose on bone formation/maturation in a rat critical-size calvarial defect model. *Journal of clinical periodontology* (2014).

21 Lee, S. S. et al. Gel Scaffolds of BMP-2-Binding Peptide Amphiphile Nanofibers for Spinal Arthrodesis. *Advanced healthcare materials* 4, 131-141 (2015).

22 Wang, E. A. et al. Recombinant human bone morphogenetic protein induces bone formation. *Proceedings of the National Academy of Sciences* 87, 2220-2224 (1990).

23 Ben-David, D. et al. Low dose BMP-2 treatment for bone repair using a PEGylated fibrinogen hydrogel matrix. *Biomaterials* 34, 2902-2910 (2013).

The invention claimed is:

1. A polymer-clay composite material comprising
   clay nanoparticles; and
   a polymer, and
   wherein
   (a) the polymer comprises phosphonate ligands; or
   (b) the polymer-clay composite further comprises linker molecules comprising a phosphonate ligand, wherein the linker molecules are arranged to be anchored to the polymer,
   wherein the phosphonate ligands comprise or consist of bisphosphonate,
   wherein the polymer-clay composite comprises between about 0.5% and about 4% polymer (w/v), and
   wherein the bisphosphonate ligands ionically bond with the clay nanoparticles in an aqueous environment to crosslink the polymer particles and form a hydrogel.

2. The polymer-clay composite material according to claim 1, further comprising water.

3. The polymer-clay composite material according to claim 2, wherein the polymer-clay composite material is in the form of a hydrogel; or
   wherein the polymer-clay composite material is in the form of a solid suitable for dissolution in water prior to use.

4. The polymer-clay composite material according to claim 1, wherein the linker molecule is anchored to the polymer.

5. The polymer-clay composite material according to claim 1, wherein the clay nanoparticle comprises or consists of layered silicate.

6. The polymer-clay composite material according to claim 1, wherein the clay nanoparticles are synthetic.

7. The polymer-clay composite material according to claim 1, wherein the clay nanoparticles have an aspect ratio of between about 1:5 and about 1:100.

8. The polymer-clay composite material according to claim 1, wherein the clay nanoparticles comprise or consist of synthetic hectorite.

9. The polymer-clay composite material according to claim 1, wherein the polymer clay composite comprises between about 0.5% and about 4% clay nanoparticles (w/v).

10. The polymer-clay composite material according to claim 1, wherein the polymer comprises or consist of a polymer selected from any of the group comprising polyacrylamide, pectin, alginate, carboxymethylcellulose, methylcellulose, PLGA, PEG, polysaccharide, starch, cellulose, chitin, alginate, hyaluronate; protein, collagen, gelatine, casein, albumin, polyvinyl alcohol (PVA), polyvinylpyrrolidone (PVP), polyetheleneglycol (PEG), polylactic acid (PLA), and polyhydroxy acid (PHA), or combinations thereof.

11. The polymer-clay composite material according to claim 1, wherein the polymer comprises or consists of glycosaminoglycan.

12. The polymer-clay composite material according to claim 11, wherein the glycosaminoglycan comprises or consists of hyaluronan (HA).

13. The polymer-clay composite material according to claim 1, wherein the polymer-clay composite material further comprise an active agent.

14. The polymer-clay composite material according to claim 1, wherein the polymer-clay composite material further comprises a cell.

* * * * *